United States Patent [19]

Hioki et al.

[11] Patent Number: 5,003,077
[45] Date of Patent: Mar. 26, 1991

[54] METHINE DYES

[75] Inventors: Takanori Hioki; Kazuhiko Matsumoto, both of Kanagawa, Japan

[73] Assignee: Fuji Photo Film Co., Ltd., Kanagawa, Japan

[21] Appl. No.: 390,059

[22] Filed: Aug. 7, 1989

Related U.S. Application Data

[63] Continuation-in-part of Ser. No. 151,756, Feb. 3, 1988, abandoned.

[30] Foreign Application Priority Data

Feb. 4, 1987 [JP] Japan .................................. 62-24375

[51] Int. Cl.$^5$ .................. C07D 235/30; C07D 473/30; C07D 215/36; C07D 401/00
[52] U.S. Cl. .................................. 548/323; 548/159; 548/181; 548/217; 548/227; 546/172; 546/174; 546/176; 546/177; 546/199; 546/271; 544/300
[58] Field of Search ............... 548/323, 159, 181, 217, 548/227; 544/300; 546/172, 174, 176, 177, 199, 271

[56] References Cited

U.S. PATENT DOCUMENTS 4,565,761  1/1986  Katagiri et al. ..................... 548/323

Primary Examiner—Mary C. Lee
Assistant Examiner—J. Richter
Attorney, Agent, or Firm—Sughrue, Mion, Zinn, Macpeak & Seas

[57] ABSTRACT

Methine dye which contains a cycloheptimidazole nucleus having a substituent at its 1-position thereof and in which the 7-membered ring moiety is substituted by a methine bond having an auxochrome, at the terminal thereof, for forming a conjugated resonance chromophoric group with the 10 $\pi$ electron series of the nucleus, showing a long absorption with one or a few methine bonds and have high light-stability and solution-stability.

10 Claims, No Drawings

METHINE DYES

CROSS-REFERENCE TO RELATED APPLICATIONS

This application is a continuation-in-part application of application Ser. No. 07/151,756, filed Feb. 3, 1988 and now abandoned.

FIELD OF THE INVENTION

The present invention relates to new methine dyes containing a cycloheptimidazole nucleus having a substituent at the 1-position thereof.

BACKGROUND OF THE INVENTION

Various dyes including non-benzene series aromatic compounds are known. Typical examples include tropilium salt compound as illustrated in Japanese Patent Application (OPI) No. 91663/86 (the term "OPI" as used herein means a "published unexamined Japanese patent application") and azulene nucleus-containing dyes as illustrated in U.S. Pat. No. 4,565,761 and Japanese Patent Application (OPI) No. 27293/86.

Among non-benzene series aromatic compounds, cycloheptimidazole nucleus-containing compounds are illustrated in Japanese Patent Publication Nos. 14500/68, 12701/70 and 17273/70, U.S. Pat. No. 3,615,607, French Patent No. 1,492,418, Japanese Patent Publication No. 27706/74, Japanese Patent Application (OPI) Nos. 260516/85 and 125384/81, Japanese Patent Publication Nos. 48558/74, 20706/65, 20707/65, 20708/65 and 20709/65, etc.

However, methine dyes such as those containing a cycloheptimidazole nucleus has a substituent at the 1-position thereof and which is a $10\pi$ electron series resonance terminal auxochrome have not been described up to the present.

SUMMARY OF THE INVENTION

An object of the present invention is to provide new methine dyes.

Specifically, the present invention provides new methine dyes which contain a cycloheptimidazole nucleus having a substituent at the 1-position thereof and in which the 7-membered ring moiety of the nucleus is substituted with a methine bond having an auxochrome, at the terminal thereof, for forming a conjugated resonance chromophoric group with the $10\pi$ electron series of the nucleus.

DETAILED DESCRIPTION OF THE INVENTION

The terminology "conjugated resonance chromophoric group" as used herein is well known in the field of organic chemistry as used, for example, in European Patent No. 192,462. The bonds via carbon atoms present between $10\pi$ electron series of the cycloheptimidazole nucleus and the auxochrome (i.e., the terminal of the conjugated resonance chromophoric group) are represented by alternate single and double bonds. However, the methine dyes of the formula (I) according to the present invention can not be represented by a single structural formula and can also be represented by the formula wherein the alternate single and double bonds via the carbon atoms are interchanged with each other.

The methine dyes of the present invention contain a cycloheptimidazole nucleus having a substituent at the 1-position thereof, and the nucleus is substituted by a methine bond having an auxochrome at the terminal thereof. The $10\pi$ electron series of the cycloheptimidazole nucleus and the auxochrome are bonded to each other via the interposed carbon atom. With respect to the bond between the cycloheptimidazole nucleus and the auxochrome via the carbon atom, there are alternate patterns of a single bond and a double bond, and the dye can be represented by the two different formulae. The two formulae indicate the limiting structures of the resonance stage, and in the two formulae, the position of the single bond and the double bond to bond the carbon atom alternates with each other. Accordingly, the cycloheptimidazole nucleus and the auxochrome form a conjugated resonant chromophoric group through the bond therebetween.

The auxochrome (which is represented by "E" hereinafter) is explained in detail.

E may have any general form which is found in methine dyes. Typically, the auxochrome is composed of nitrogen or chalcogen atoms and resonates between the charged state and the non-charged state in a dye. For example, the auxochrome E may be any state of the auxochromes to be found in cyanine, merocyanine, oxonole, pyrylium or thiapyrylium dyes. However, the auxochrome in the dyes of the present invention needs not to be limited to only these groups. Although not as general, other auxochromes containing other atoms such as a phosphorus or boron atom can also be used in the present invention. For example, 2-triphenylphosphoro-1,3-cyclopentadien-5-yl as one example of the auxochrome may be mentioned.

The general characteristic of the methine dyes of the present invention (which will be referred to as "dyes" briefly hereinafter, as the case may be) is understood from the standpoint of the production of the dyes. The cycloheptimidazole nucleus to be used as the starting material for the production of the dyes of the present invention has a positive charge and is activated at at least one nucleic carbon atom of the cycloheptimidazole nucleus or its methyl substituent as a reactive position. The activated nucleic carbon atoms in the cycloheptimidazole nucleus can be considered to be a carbo-cation in one resonant state. When the same carbon atom is methyl-substituted, the carbo-anion is formed by the de-protonation of the methyl-substituent in one resonant state. From the carbo-cation (positive) or carbo-anion (negative) part of the cycloheptimidazole nucleus, the methine bond is formed.

Various embodiments which may correspond with the above-mentioned general explanation are practical, and some typical embodiments are described hereinafter so as to explain the present invention.

The dyes of the present invention are preferably represented by the alternate resonant states of the following formula (I).

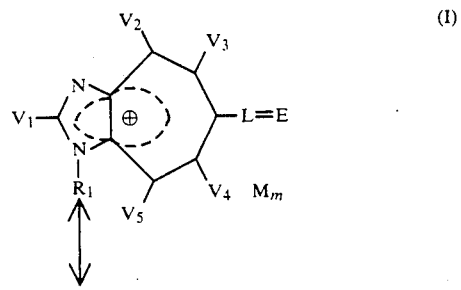

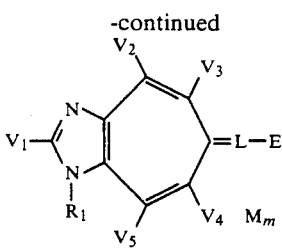

In the formula (I), E represents an auxochrome; L represents a methine bond; $R_1$ represents a substituted or unsubstituted alkyl group, a substituted or unsubstituted aryl group or a heterocyclic group. The methine bond comprises methine groups (which may be substituted) and preferably means a combination of up to seven methine groups.

$V_1$, $V_2$, $V_3$, $V_4$ and $V_5$ each represents a hydrogen atom, a halogen atom or a substituted or unsubstituted alkyl group, a substituted or unsubstituted acyl group, a substituted or unsubstituted acyloxy group, a substituted or unsubstituted alkoxycarbonyl group, a substituted or unsubstituted carbamoyl group, a substituted or unsubstituted sulfamoyl group, a carboxyl group, a cyano group, a hydroxyl group, a substituted or unsubstituted amino group, a substituted or unsubstituted acylamino group, a substituted or unsubstituted alkoxy group, a substituted or unsubstituted alkylthio group, a substituted or unsubstituted alkylsulfonyl group, a sulfonic acid group or a substituted or unsubstituted aryl group, or two of $V_1$ to $V_5$ which are bonded to the adjacent carbon atoms may form a condensed ring.

M represents an electric charge-equilibrating paired ion, and m represents 0 or 1.

In formula (I), although the position of the methine bond L is represented in the 6-position as one example, the bond may be bonded to any other position (which may be selected from the 4-, 5-, 7- and 8-positions). Preferably, the bond is bonded to the 4-, 6- or 8-position, more preferably to the 4- or 6-position.

Of the dyes of the formula (I), those represented by the following formulae (II) to (V) are preferred.

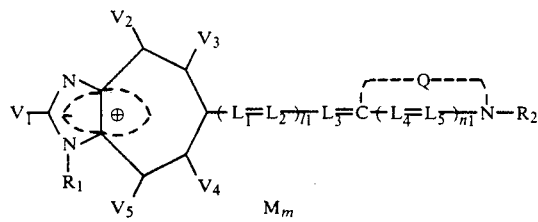

in which
$R_1$, $V_1$ to $V_5$, M and m have the same meanings as in the formula (I);

the position of the methine bond may be any of the 4-, 5-, 6-, 7- or 8-position, just as in the case of the formula (I);

Q represents an atomic group necessary for forming a 5-membered or 6-membered nitrogen-containing hetero-ring;

$L_1$, $L_2$, $L_3$, $L_4$ and $L_5$ each represents an optionally substituted methine group;

$R_2$ represents a substituted or unsubstituted alkyl group;

$l_1$ represents an integer of from 0 to 3;

$n_1$ represents 0 or 1;

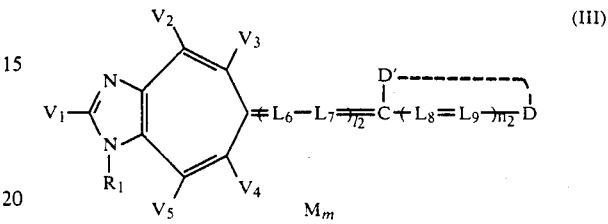

in which $R_1$, $V_1$ to $V_5$, M and m have the same meanings as in the formula (I);

the position of the methine bond may be any of the 4-, 5-, 6-, 7- or 8-position, just as in the case of the formula (I);

D and D' each represents an atomic group necessary for forming an acidic nucleus, which may be acyclic or cyclic;

$L_6$, $L_7$, $L_8$ and $L_9$ have the same meanings as $L_1$, $L_2$, $L_3$, $L_4$ and $L_5$;

$l_2$ represents an integer of from 0 to 3;

$n_2$ represents 0 or 1.

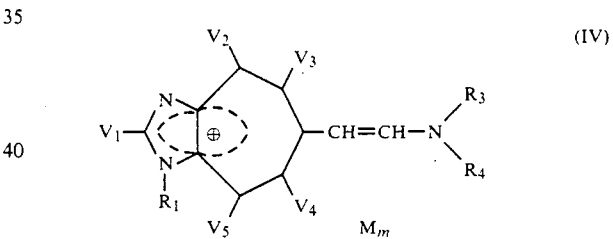

in which $R_1$, $V_1$ to $V_5$, M and m have the same meanings as in the formula (I);

the position of the methine bond may be any of the 4-, 5-, 6-, 7- or 8-position, just as in the case of the formula (I);

$R_3$ and $R_4$ each represents a substituent which is generally found in tertiary amines; and these $R_3$ and $R_4$ are derived from the substituents of the tertiary amines used in the production of the dyes of the formula (IV) and therefore may be any substituents generally found in tertiary amines.

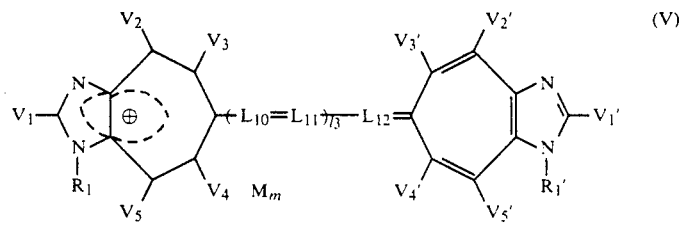

in which $R_1$, $V_1$ to $V_5$, M and m have the same meanings as in the formula (I);

formula (I);

$R_1'$ has the same meaning as $R_1$;

$V_1'$ to $V_5'$ have the same meanings as $V_1$ to $V_5$;

the position of the methine bond may be any of the 4-, 5-, 6-, 7- or 8-position, just as in the case of the formula (I);

$L_{10}$, $L_{11}$ and $L_{12}$ have the same meanings as $L_1$, $L_2$, $L_3$, $L_4$ and $L_5$;

$l_3$ represents an integer of from 0 to 3.

The formulae (I) to (V) are explained in detail hereinafter.

$R_1$ and $R_1'$ each are preferably an unsubstituted alkyl group having 18 or less carbon atoms (e.g., a methyl group, an ethyl group, a propyl group, a butyl group, a pentyl group, an octyl group, a decyl group, a dodecyl group, an octadecyl group, etc.); or a substituted alkyl group having 18 or less carbon atoms, the substituent being, for example, a carboxyl group, a sulfo group, a cyano group, a halogen atom (e.g., a fluorine atom, a chlorine atom, a bromine atom, etc.), a hydroxyl group, an alkoxycarbonyl group having 8 or less carbon atoms (e.g., a methoxycarbonyl group, an ethoxycarbonyl group, a phenoxycarbonyl group, a benzyloxycarbonyl group, etc.), an alkoxy group having 8 or less carbon atoms (e.g., a methoxy group, an ethoxy group, a benzyloxy group, a phenethyloxy group, etc.), a monocyclic aryloxy group having 10 or less carbon atoms (e.g., a phenoxy group, a p-tolyloxy group, etc.), an acyloxy group having 3 or less carbon atoms (e.g., an acetyloxy group, a propionyloxy group, etc.), an acyl group having 8 or less carbon atoms (e.g., an acetyl group, a propionyl group, a benzoyl group, a mesyl group, etc.), a carbamoyl group (e.g., a carbamoyl group, an N,N-dimethylcarbamoyl group, a morpholinocarbonyl group, a piperidinocarbonyl group, etc.), a sulfamoyl group (e.g., a sulfamoyl group, an N,N-dimethylsulfamoyl group, a morpholinosulfonyl group, a piperidinosulfonyl group, etc.), an aryl group having 10 or less carbon atoms (e.g., a phenyl group, a 4-chlorophenyl group, a 4-methylphenyl group, an α-naphthyl group, etc.), etc.; or an aryl group (e.g., a phenyl group, a 2-naphthyl group, etc.); or a substituted aryl group (e.g., a 4-carboxyphenyl group, a 4-sulfophenyl group, a 3-chlorophenyl group, a 3-methylphenyl group, etc.); or a heterocyclic group (e.g., a 2-pyridyl group, a 2-thiazolyl group, etc.).

Especially preferably, these are independently an unsubstituted alkyl group (e.g., a methyl group, an ethyl group, etc.) or a sulfoalkyl group (e.g., a 2-sulfoethyl group, a 3-sulfo propyl group, a 4-sulfobutyl group, etc.).

More preferably, these are methyl groups.

As to $V_1$, $V_2$, $V_3$, $V_4$, $V_5$, $V_1'$, $V_2'$, $V_3'$, $V_4'$ and $V_5'$, a hydrogen atom, a halogen atom (e.g., a chlorine atom, a fluorine atom, a bromine atom, etc.), an unsubstituted alkyl group having 10 or less carbon atoms (e.g., a methyl group, an ethyl group, etc.), a substituted alkyl group having 18 or less carbon atoms (e.g., a benzyl group, an α-naphthylmethyl group, a 2-phenylethyl group, a trifluoromethyl group, etc.), an acyl group having 10 or less carbon atoms (e.g., an acetyl group, a benzoyl group, a mesyl group, etc.), an acyloxy group having 10 or less carbon atoms (e.g., an acetyloxy group, etc.), an alkoxycarbonyl group having 10 or less carbon atoms (e.g., a methoxycarbonyl group, an ethoxycarbonyl group, a benzyloxycarbonyl group, etc.), a substituted or unsubstituted carbamoyl group (e.g., a carbamoyl group, an N,N-dimethylcarbamoyl group, a morpholinocarbonyl group, a piperidinocarbonyl group, etc.), a substituted or unsubstituted sulfamoyl group (e.g., a sulfamoyl group, an N,N-dimethylsulfamoyl group, a morpholinosulfonyl group, a piperidinosulfonyl group, etc.), a carboxyl group, a cyano group, a hydroxyl group, an amino group, an acylamino group having 8 or less carbon atoms (e.g., an acetylamino group, etc.), an alkoxy group having 10 or less carbon atoms (e.g., a methoxy group, an ethoxy group, a benzyloxy group, etc.), an alkylthio group (e.g., an ethylthio group, etc.), an alkylsulfonyl group (e.g., a methylsulfonyl group, etc.), a sulfonic acid group or an aryl group (e.g., a phenyl group, a tolyl group, etc.) are preferred. In addition, two of these $V_1$ to $V_5$ (as well as $V_1'$ to $V_5'$) which are bonded to the adjacent carbon atoms may be bonded to each other to form a benzene ring. Furthermore, they may also be bonded to each other to form a hetero ring (e.g., a pyrrole ring, a thiophene ring, a furan ring, a pyridine ring, an imidazole ring, a triazole ring, a thiazole ring, etc.).

For $V_2$, $V_3$, $V_4$, $V_5$, $V_2'$, $V_3'$, $V_4'$ and $V_5'$, hydrogen atoms are preferred. $V_1$ (as well as $V_1'$) is preferably a hydrogen atom, a chlorine atom, an alkoxy group (e.g., a methoxy group, etc.), an alkylthio group (e.g., a methylthio group, etc.) or an aryl group (e.g., a phenyl group, etc.).

$M_m$ is present in the formula to show the presence or absence of the cation or anion, when the ionic charge of the dye must be neutralized. The matter as to whether a certain dye is cationic or anionic or as to whether it does not substantially have any ionic charge depends upon the auxochrome and the substituents in the dye. The pair ion can easily be exchanged after the dye has been produced. Typical cations are an ammonium ion and an alkali metal ion; and the anion specifically may be either an inorganic anion or an organic anion, for example, including a halogen anion (e.g., a fluoride ion, a chloride ion, a bromide ion, an iodide ion, etc.), a substituted arylsulfonic acid ion (e.g., a p-toluenesulfonic acid ion, a p-chlorobenzenesulfonic acid ion, etc.), an aryl-disulfonic acid ion (e.g., a 1,3-benzenedisulfonic acid ion, a 1,5-naphthalene-disulfonic acid ion, a 2,6-naphthalene-disulfonic acid ion, etc.), an alkylsulfuric acid ion (e.g., a methylsulfuric acid ion, etc.), a sulfuric acid ion, a thiocyanic acid ion, a perchloric acid ion, a tetrafluoroboric acid ion, a picric acid ion, an acetic acid ion, a trifluorosulfonic acid ion, etc. Preferably, it is an iodide ion.

The nucleus formed by Q includes, for example, a thiazole nucleus (such as a thiazole nucleus (e.g., a thiazole, a 4-methylthiazole, 4-phenylthiazole, a 4,5-dimethylthiazole, 4,5-diphenylthiazole, etc.), a benzothiazole nucleus (e.g., a benzothiazole, a 4-chlorobenzothiazole, a 5-chlorobenzothiazole, a 6-chlorobenzothiazole, a 5-nitrobenzothiazole, a 4-methylbenzothiazile, a 5-methylbenzothiazole, a 6-methylbenzothiazole, a 5-bromobenzothiazole, a 6-bromobenzothiazole, a 5-iodobenzothiazole, a 5-phenylbenzothiazole, a 5-methoxybenzothiazole, a 6-methoxybenzothiazole, a 5-ethoxybenzothiazole, a 5-ethoxycarbonylbenzothiazole, a 5-carboxybenzothiazole, a 5-phenethylbenzothiazole, a 5-fluorobenzothiazole, a 5-chloro-6-methylbenzothiazole, a 5,6-dimethylbenzothiazole, a 5,6-dimethoxybenzothiazole, a 5-hydroxy-6-methylbenzothiazole, a tetrahydrobenzothiazole, a 4-phenylbenzothiazole, etc.), a naphthothiazole nucleus (e.g., a naphtho[2,1-d]thiazole, a naphtho[1,2-d]thiazole, naphtho[2,3-d]thiazole, a 5-methoxnaphtho[1,2-d]thiazole, a 7-ethoxynaphtho[2,1-d]thiazole, a 8- methoxynaphtho[2,1-d]thiazole, a 5-methoxynaphtho[2,3-d]thiazole, etc.), etc.); a thiazoline nucleus (e.g., a thiazoline, a 4-methylthiazoline, a 4-nitrothiazoline, etc.); an oxazole nucleus (such as an oxazole nucleus (e.g., an oxazole, a 4-methyloxazole, a 4-nitrooxazole, a 5-methyloxazole, a 4-phenyloxazole, a 4,5-diphenyloxazole, a 4-ethyloxazole, etc.), a benzoxazole nucleus (e.g., a benzoxazole, a 5-chlorobenzoxazole, a 5-methylbenzoxazole, a 5-bromobenzoxazole, a 5-fluorobenzoxazole, a 5-phenylbenzoxazole, a 5-methoxybenzoxazole, a 5-nitrobenzoxazole, a 5-trifluoromethylbenzoxazole, a 5-hydroxybenzoxazole, a 5-carboxybenzoxazole, a 6-methylbenzoxazole, a 6-chlorobenzoxazole, a 6-nitrobenzoxazole, a 6-methoxybenzoxazole, a 6-hydroxybenzoxazole, a 5,6-dimethylbenzoxazole, a 4,6-dimethylbenzoxazole, a 5-ethoxybenzoxazole, etc.), a naphthoxazole nucleus (e.g., a naphtho[2,1-d]oxazole, a naphtho[1,2-d]oxazole, a naphtho[2,3-d]oxazole, a 5-nitronaphtho[2,1-d]oxazole, etc.), etc.); an oxazoline nucleus (e.g., a 4,4-dimthyloxazoline, etc.); a selenazole nucleus (such as a selenazole nucleus (e.g., a 4-methylselenazole, a 4-nitroselenazole, a 4-phenylselenazole, etc.), a benzoselenazole nucleus (e.g., a benzoselenazole, a 5-chlorobenzoselenazole, a 5-nitrobenzoselenazole, a 5-methoxybenzoselenazole, a 5-hydroxybenzoselenazole, a 6-nitrobenzoselenazole, a 5-chloro-6-nitrobenzoselenazole, a 5,6-dimethylbenzoselenazole, etc.), a naphthoselenazole nucleus (e.g., a naphtho[2,1-d]selenazole, a naphtho[1,2-d]selenazole, etc.), etc.); a selenazoline nucleus (e.g., a selenazoline, 4-methylselenazoline, etc.); a tellurazole nucleus (such as a tellurazole nucleus (e.g., a tellurazole, a 4-methyltellurazole, a 4-phenyltellurazole, etc.), a benzotellurazole nucleus (e.g., a benzotellurazole, a 5-chlorobenzotellurazole, a 5-methylbenzotellurazole, a 5,6-dimethylbenzotellurazole, a 6-methoxybenzotellurazole, etc.), a naphthotellurazole nucleus (e.g., a naphtho[2,1-d]tellurazole, a naphtho[1,2-d]tellurazole, etc.), etc.); a tellurazoline nucleus (e.g., a tellurazoline, a 4-methyltellurazoline, etc.); a 3,3-dialkylindolenine nucleus (e.g., a 3,3-dimethylindolenine, a 3,3-diethylindolenine, 3,3-dimethyl-5-cyanoindolenine, a 3,3-dimethyl-6-nitroindolenine, a 3,3-dimethyl-5-nitroindolenine, a 3,3-dimethyl-5-methoxyindolenine, a 3,3,5-trimethylindolenine, a 3,3-dimethyl-5-chloroindolenine, etc.); an imidazole nucleus (such as an imidazole nucleus (e.g., a 1-alkylimidazole, a 1-alkyl-4-phenylimidazole, etc.), a benzimidazoline nucleus (e.g., a 1-alkylbenzimidazole, a 1-alkyl-5-chlorobenzimidazole, a 1-alkyl-5,6-dichlorobenzimidazole, a 1-alkyl-5-methoxybenzimidazole, a 1-alkyl-5-cyanobenzimidazole, a 1-alkyl-5-fluorobenzimidazole, a 1-alkyl-5-trifluoromethylbenzimidazole, 1-alkyl-6-chloro-5-cyanobenzimidazole, a 1-alkyl-6-chloro-5-trifluoromethylbenzimidazole, a 1-allyl-5,6-dichlorobenzimidazole, a 1-allyl-5-chlorobenzimidazole, a 1-arylimidazole, a 1-arylbenzimidazole, a 1-aryl-5-chlorobenzimidazole, a 1-aryl-5,6-dichlorobenzimidazole, a 1-aryl-5-methoxybenzimidazole, a 1-aryl-5-cyanobenzimidazole, etc.), a naphthoimidazole nucleus (e.g., a 1-alkylnaphtho[1,2-d]imidazole, a 1-arylnaphtho[1,2-d]imidazole, etc.), etc.; in which the above-mentioned alkyl group is preferably one having from 1 to 8 carbon atoms, for example, including an unsubstituted alkyl group (e.g., a methyl group, an ethyl group, a propyl group, an isopropyl group, a butyl group, etc.) or a hydroxyalkyl group (e.g., a 2-hydroxyethyl group, a 3-hydroxypropyl group, etc.); and especially preferably the alkyl group is a methyl group or an ethyl group; and the above-mentioned aryl group is a phenyl group, a halogen (e.g., a chloro)-substituted phenyl group, an alkyl (e.g., methyl)-substituted phenyl group, an alkoxy (e.g., methoxy)-substituted phenyl group, etc.); a pyridine nucleus (e.g., a 2-pyridine, a 4-pyridine, a 5-methyl-2-pyridine, a 3-methyl-4-pyridine, etc.), a quinoline nucleus (such as a quinoline nucleus (e.g., a 2-quinoline, a 3-methyl-2-quinoline, a 5-ethyl-2-quinoline, a 6-methyl-2-quinoline, a 6-nitro-2-quinoline, an 8-fluoro-2-quinoline, a 6-methoxy-2-quinoline, a 6-hydroxy-2-quinoline, an 8-chloro-2-quinoline, a 4-quinoline, a 6-ethoxy-4-quinoline, a 6-nitro-4-quinoline, an 8-chloro-4-quinoline, an 8-fluoro-4-quinoline, an 8-methyl-4-quinoline, an 8-methoxy-4-quinoline, a 6-methyl-4-quinoline, a 6-methoxy-4-quinoline, a 6-chloro-4-quinoline, etc.), as isoquinoline nucleus (e.g., a 6-nitro-1-isoquinoline, a 3,4-dihydro-1-isoquinoline, a 6-nitro-3-isoquinoline, etc.), etc.; an imidazo[4,5-b]quinoxaline nucleus (e.g., a 1,3-diethylimidazo[4,5-b]quinoxaline, a 6-chloro-1,3-diallylimidazo[4,5-b]quinoxaline, etc.), an oxadiazole nucleus, a thiadiazole nucleus, a tetrazole nucleus, a pyrimidine nucleus, etc.

Benzothiazole nuclei and benzoxazole nuclei are especially preferred of these groups.

$R_2$ may be in the form of a quaternary substituent of any cyanine dyes. For example, the examples of the above-mentioned unsubstituted alkyl groups and substituted alkyl groups for $R_1$ (or $R_1'$) are preferably applied thereto.

D and D' each represents an atomic group necessary for forming an acidic nucleus, and these may be in any form of acid nuclei of general merocyanine dyes. Preferably, D is a cyano group, a sulfo group or a carbonyl group; and D' is the remaining atomic group necessary for forming an acidic group.

When the acidic nucleus is acyclic, or that is, D and D' are independent groups, the terminal of the methine bond is a mannonitrile, alkylsulfonylacetonitrile, cyanomethylbenzofuranylketone or cyanomethylphenylketone or the like group, D and D' together form a 5-membered or 6-membered hetero-ring comprising carbon, nitrogen and chalcogen (typically oxygen, sulfur, selenium and tellurium) atoms. Preferably D and D' together complete anyone of the following nuclei: 2-pyrazolin-5-one, pyrazolidine-3,5-dione, imidazolin-5-one, hydantoin, 2- or 4-thiohydantoin, 2-iminoxazolidin-4-one, 2-oxazolin-5-one, 2-thioxoxazolidine-2,4-dione, isoxazolin-5-one, 2-thiazolin-4-one, thiazolidin-4-one, thiazolidine-2,4-dione, rhodanine, thiazolidine-2,4-dithione, isorhodanine, indane-1,3-dione, thiophen-3-one, thiopen-3-one-1,1-dioxide, indolin-2-one, indolin-3-one, indazolin-3-one, 2-omxoindazolinium, 3-oxoindazolinium, 5,7-dioxo-6,7-dihydrothiazolo[3,2-d]pyrimidine, cyclohexane-1,3-dione, 3,4-dihydroisoquinolin-4-one, 1,3-dioxane-4,6-dione, barbituric acid, 2-thiobarbituric acid, chroman-2,4-dione, indazolin-2-one and pyrido[1,2-a]pyrimidine-1,3-dione nuclei.

More preferred are 1,3-dialkylbarbituric acid, 1,3-dialkyl-2-thiobarbituric acid and 3-alkylrhodanine nuclei, in which the alkyl group is preferably an unsubstituted alkyl group.

The substituent as bonded to the nitrogen atom contained in the above-mentioned acidic nuclei is preferably a hydrogen atom, an alkyl group having from 1 to 18, preferably from 1 to 7, especially preferably from 1 to 4, carbon atoms (e.g., a methyl group, an ethyl group, a propyl group, an isopropyl group, a butyl group, an isobutyl group, a hexyl group, an octyl group, a dodecyl group, an octadecyl group, etc.); a substituted alkyl group (such as an aralkyl group (e.g., a benzyl group, a 2-phenylethyl group, etc.), a hydroxyalkyl group (e.g., a 2-hydroxyethyl group, a 3-hydroxypropyl group, etc.), a carboxyalkyl group (e.g., a 2-carboxyethyl group, a 3-carboxypropyl group, a 4-carboxybutyl group, a carboxymethyl group, etc.), an alkoxyalkyl group (e.g., a 2-methoxyethyl group, a 2-(2-methoxyethoxy)ethyl group, etc.), a sulfoalkyl group (e.g., a 2-sulfoethyl group, a 3-sulfopropyl group, a 3-sulfobutyl group, a 4-sulfobutyl group, a 2-(3-sulfopropoxy)ethyl group, a 2-hydroxy-3-sulfopropyl group, a 3-sulfopropoxyethoxyethyl group, etc.), a sulfatoalkyl group (e.g., a sulfatopropyl group, a 4-sulfatobutyl group, etc.), a heterocyclic-substituted alkyl group (e.g., a 2-(pyrrolidin-2-on-1-yl)ethyl group, a tetrahydrofurfuryl group, a 2-morpholinoethyl group, etc.), a 2-acetoxyethyl group, a carbomethoxymethyl group, a 2-methylsulfonylaminoethyl group, etc.); an allyl group; an aryl group (e.g., a phenyl group, a 2-naphthyl group, etc.); a substituted aryl group (e.g., a 4-carboxyphenyl group, a 4-sulfophenyl group, a 3-chlorophenyl group, a 3-methylphenyl group, etc.); a heterocyclic group (e.g., a 2-pyridyl group, a 2-thiazolyl group, etc.), etc.

$R_3$ and $R_4$ may be the same or different from each other; and these are independently preferably selected from the examples of the unsubstituted alkyl groups and substituted alkyl groups as referred to for the abovementioned $R_1$, or are independently preferably a cyano group, an alkoxy group (e.g., a methoxy group, an ethoxy group, etc.), an aryloxy group (e.g., a phenoxy group, etc.), an alkoxycarbonyl group (e.g., an ethoxycarbonyl group, etc.), etc.

In addition, $R_3$ and $R_4$ may be bonded to each other to form a hetero-ring other than an aromatic hetero-ring.

For example, the hetero-ring is preferably a pyrrolidine, a piperidine, a morpholine, a piperazine, a tetrahydropyridine, a dihydropyridine, a tetrahydroquinoline, etc. ring.

More preferably, $R_3$ and $r_4$ are both ethyl groups.

The methine group represented by $L_1$, $L_2$, $L_3$, $L_4$, $L_5$, $L_6$, $L_7$, $L_8$, $L_9$, $L_{10}$, $L_{11}$ or $L_{12}$ may optionally be substituted by a substituted or unsubstituted alkyl group (e.g., a methyl group, an ethyl group, etc.), a substituted or unsubstituted aryl group (e.g., a phenyl group, etc.) and/or a halogen atom (e.g., a chlorine atom, a bromine atom, etc.). In addition, this may form a ring together with another methine group, or may form a ring together with an auxochrome.

Specific examples of the methine dyes of the present invention are described below. However, they are not intended to limit the scope of the present invention.

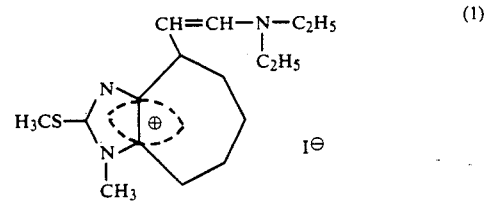   (1)

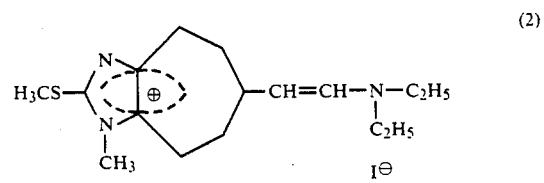   (2)

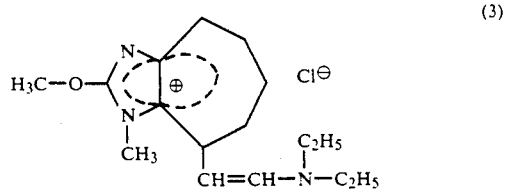   (3)

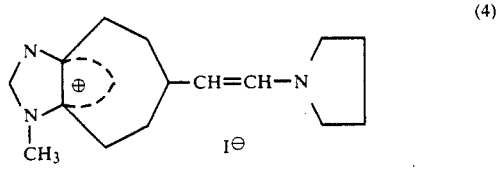   (4)

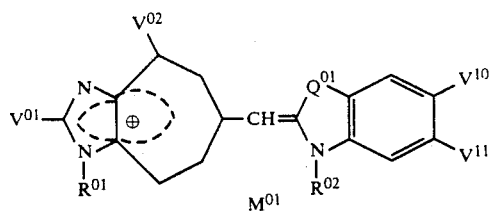

| Compound | $V^{01}$ | $V^{02}$ | $R^{01}$ | $Q^{01}$ | $R^{02}$ | $V^{10}$ | $V^{11}$ | $M^{01}$ |
|---|---|---|---|---|---|---|---|---|
| (5) | H | H | $CH_3$ | S | $CH_3$ | H | H | $I^\ominus$ |
| (6) | H | H | $CH_3$ | S | $C_2H_5$ | H | H | $I^\ominus$ |
| (7) | $SCH_3$ | H | $CH_3$ | S | $C_2H_5$ | H | H | $I^\ominus$ |
| (8) | Cl | H | $CH_3$ | S | $C_2H_5$ | H | H | $I^\ominus$ |
| (9) | $OCH_3$ | H | $CH_3$ | S | $C_2H_5$ | H | H | $I^\ominus$ |
| (10) | $SCH_3$ | H | $CH_3$ | S | $(CH_2)_4SO_3^\ominus$ | H | H | — |
| (11) | $SCH_3$ | H | $(CH_2)_4SO_3^\ominus$ | S | $C_2H_5$ | H | H | — |
| (12) | H | H | $(CH_2)_4SO_3^\ominus$ | S | $(CH_2)_4SO_3H.N(C_2H_5)_3$ | H | H | — |
| (13) | $SCH_3$ | H | $C_2H_5$ | S | $nC_3H_7$ | $CH_3$ | H |  |
| (14) | $SCH_3$ | H | $CH_3$ | O | $C_2H_5$ | H | H | $I^\ominus$ |

-continued

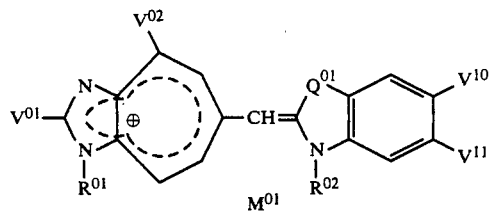

| Compound | $V^{01}$ | $V^{02}$ | $R^{01}$ | $Q^{01}$ | $R^{02}$ | $V^{10}$ | $V^{11}$ | $M^{01}$ |
|---|---|---|---|---|---|---|---|---|
| (15) | H | CH(CH$_3$)$_2$ | CH$_3$ | O | C$_2$H$_5$ | H | H | I$^\ominus$ |
| (16) | OCH$_3$ | H | C$_2$H$_5$ | O | C$_2$H$_5$ | H | phenyl | Cl$^\ominus$ |
| (17) | SCH$_3$ | H | CH$_3$ | N—C$_2$H$_5$ | C$_2$H$_5$ | Cl | Cl | I$^\ominus$ |
| (18) | H | H | C$_2$H$_5$ | N—C$_2$H$_5$ | (CH$_2$)$_4$SO$_3^\ominus$ | Cl | CN | — |
| (19) | Cl | H | (CH$_2$)$_4$SO$_3^\ominus$ | N—C$_2$H$_5$ | (CH$_2$)$_4$SO$_3$Na | Cl | CF$_3$ | — |
| (20) | SCH$_3$ | H | CH$_3$ | N—(CH$_2$)$_2$OH | CH$_3$ | Cl | Cl | Br$^\ominus$ |
| (21) | H | H | CH$_3$ | C(CH$_3$)$_2$ | CH$_3$ | H | H | I$^\ominus$ |
| (22) | SCH$_3$ | H | (CH$_2$)$_3$SO$_3^\ominus$ | C(CH$_3$)$_2$ | CH$_3$ | Cl | H | — |
| (23) | SCH$_3$ | H | nC$_5$H$_{11}$ | S | C$_2$H$_5$ | H | H | I$^\ominus$ |
| (24) | H | H | nC$_3$H$_7$ | S | C$_2$H$_5$ | H | H | I$^\ominus$ |

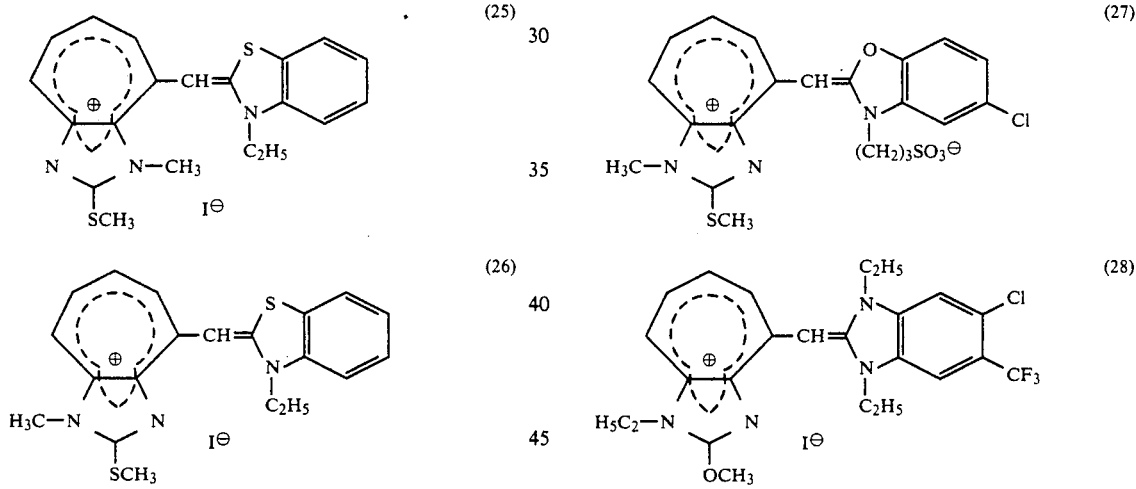

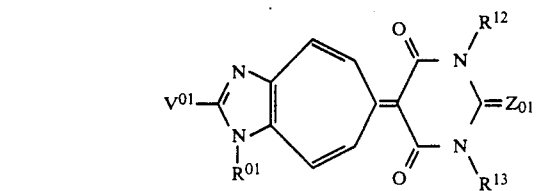

| Compound | $V^{01}$ | $R^{01}$ | $Z_{01}$ | $R^{12}$ | $R^{13}$ |
|---|---|---|---|---|---|
| (29) | H | CH$_3$ | S | C$_2$H$_5$ | C$_2$H$_5$ |
| (30) | SCH$_3$ | CH$_3$ | S | C$_2$H$_5$ | C$_2$H$_5$ |
| (31) | SCH$_3$ | CH$_3$ | O | nC$_4$H$_9$ | nC$_4$H$_9$ |
| (32) | Cl | (CH$_2$)$_4$SO$_3$Na | S | CH$_3$ | CH$_3$ |
| (33) | phenyl | CH$_3$ | S | (CH$_2$)$_4$SO$_3$H.N-pyridyl | C$_2$H$_5$ |

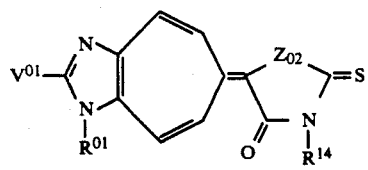

| Compound | $V^{01}$ | $R^{01}$ | $Z_{02}$ | $R^{14}$ |
|---|---|---|---|---|
| (34) | H | $CH_3$ | S | $C_2H_5$ |
| (35) | H | $C_2H_5$ | O | $CH_2COOC_2H_5$ |
| (36) | $SCH_3$ | $(CH_2)_3SO_3K$ | $NC_2H_5$ |  |
| (37) | $SCH_3$ | $C_2H_5$ | S | $CH_2COOH$ |

(41) 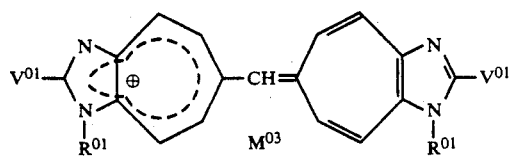 $CH_3$ $Br^{\ominus}$ (38)

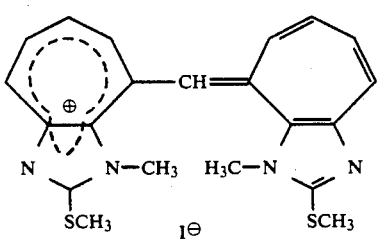

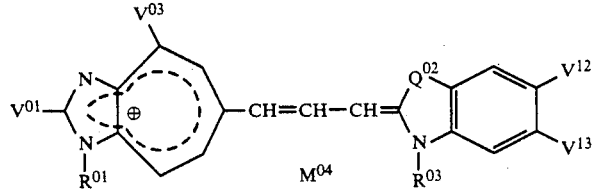

| Compound | $V^{01}$ | $R^{01}$ | $M^{03}$ |
|---|---|---|---|
| (42) | $SCH_3$ | $CH_3$ | $I^{\ominus}$ |
| (43) | $SCH_3$ | $(CH_2)_4SO_3^{\ominus}$ | $Na^{\oplus}$ |
| (44) | H | $C_2H_5$ |  |
| (45) | $SCH_3$ | $CH_2COOH$ | $I^{\ominus}$ |

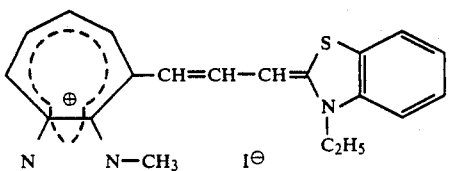

| Compound | $V^{01}$ | $R^{01}$ | $Q^{02}$ | $V^{12}$ | $V^{13}$ | $R^{03}$ | $M^{04}$ |
|---|---|---|---|---|---|---|---|
| (46) | $SCH_3$ | $CH_3$ | S | H | H | $C_2H_5$ | $I^{\ominus}$ |
| (47) | Cl | $CH_3$ | O | H | phenyl | $(CH_2)_4SO_3^{\ominus}$ | — |
| (48) | H | $(CH_2)_4SO_3^{\ominus}$ | S | $CH_3$ | $CH_3$ | $C_2H_4OCH_3$ | — |
| (49) | $OCH_3$ | $CH_3$ | S | $OCH_3$ | $OCH_3$ | $nC_3H_7$ | $I^{\ominus}$ |

(50)

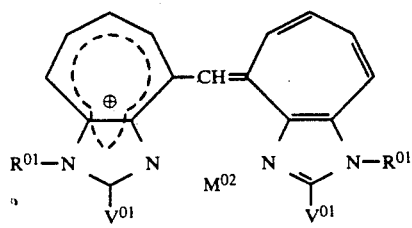

| Compound | $V^{01}$ | $R^{01}$ | $M^{02}$ |
|---|---|---|---|
| (39) | $SCH_3$ | $CH_3$ | $I^{\ominus}$ |
| (40) | Cl | $CH_3$ | $I^{\ominus}$ |

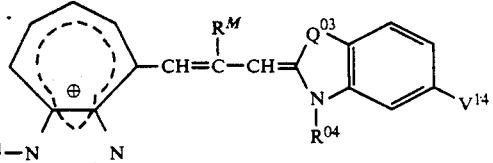

| Compound | $R^{01}$ | $R^M$ | $Q^{03}$ | $V^{14}$ | $R^{04}$ | $M^{05}$ |
|---|---|---|---|---|---|---|

|     | (51) | CH₃ | CH₃ | O | | (CH₂)₄SO₃⁻ | — |
|     | (52) | CH₃ | H | Se | H | C₂H₅ | Cl⁻ |
|     | (53) | CH₃ | C₂H₅ | C(CH₃)₂ | H | (CH₂)₃SO₃⁻ | — |
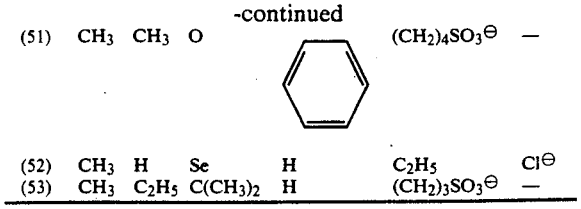
| Compound | V⁰¹ | R⁰¹ | V⁰³ | Z₀₂ | R¹⁴ | R¹⁵ |
|---|---|---|---|---|---|---|
| (54) | H | CH₃ | H | S | C₂H₅ | C₂H₅ |
| (55) | SCH₃ | C₂H₅ | H | O | nC₄H₉ | nC₄H₉ |
| (56) | phenyl | (CH₂)₃SO₃K | H | S | CH₃ | CH₃ |
| (57) | piperidino | CH₃ | H | S | (CH₂)₃SO₃Na | CH₃ |
| (58) | OCH₃ | CH₃ | CH(CH₃)₂ | S | CH₃ | nC₄H₉ |
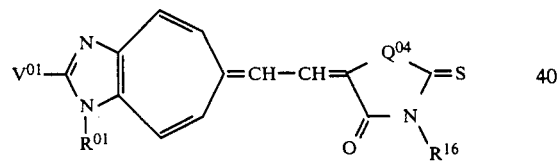
| Compound | V⁰¹ | R⁰¹ | Q⁰⁴ | R¹⁶ |
|---|---|---|---|---|
| (59) | SCH₃ | CH₃ | S | C₂H₅ |
| (60) | SCH₃ | CH₃ | S | CH₂COOH |
| (61) | Cl | CH₃ | O | 2-pyridyl |
| (62) | SCH₃ | C₂H₅ | N(CH₂)₂O(CH₂)₂OH | 2-pyridyl |
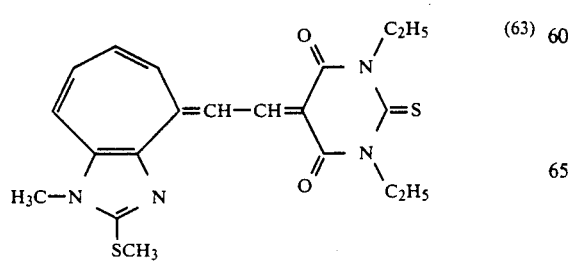
(63)
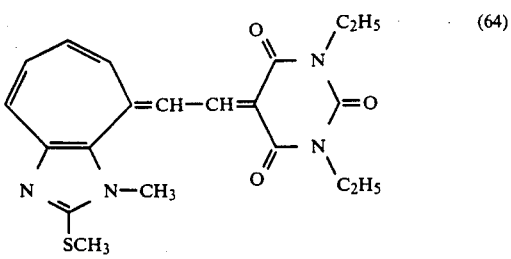
(64)
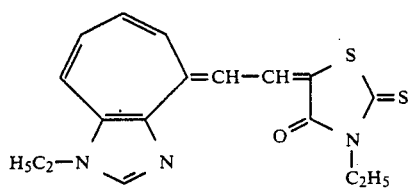
(65)
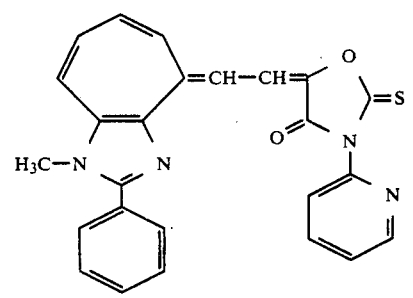
(66)
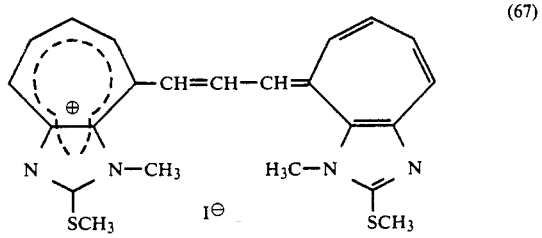
(67)

-continued
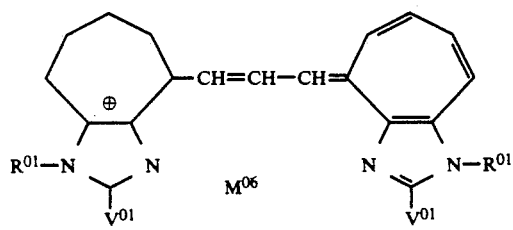
| Compound | $V^{01}$ | $R^{01}$ | $M^{06}$ |
|---|---|---|---|
| (68) | $SCH_3$ | $CH_3$ | $I^\ominus$ |
| (69) | Cl | $CH_3$ | $Br^\ominus$ |
| (70) |  | $CH_3$ | $I^\ominus$ |
-continued
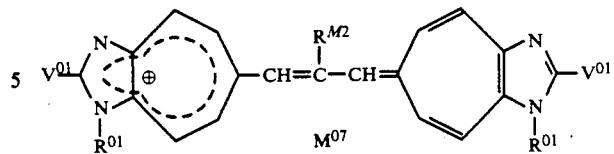
| Compound | $V^{01}$ | $R^{01}$ | $R^{M2}$ | $M^{07}$ |
|---|---|---|---|---|
| (71) |  | $CH_3$ | H | $I^\ominus$ |
| (72) | $SCH_3$ | $CH_3$ | H | $I^\ominus$ |
| (73) | $SCH_3$ | $CH_2COOH$ | $CH_3$ | $Br^\ominus$ |
| (74) | $SCH_3$ | $CH_3$ |  | $I^\ominus$ |
(75)
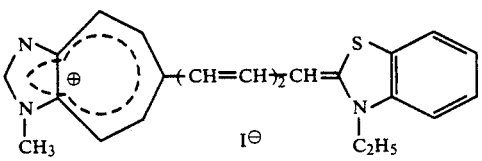
(76)
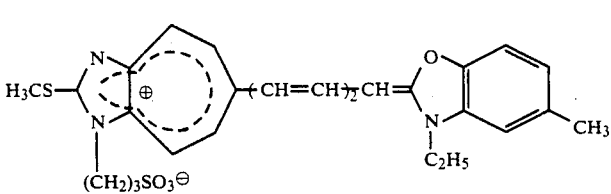
(77)
(78)
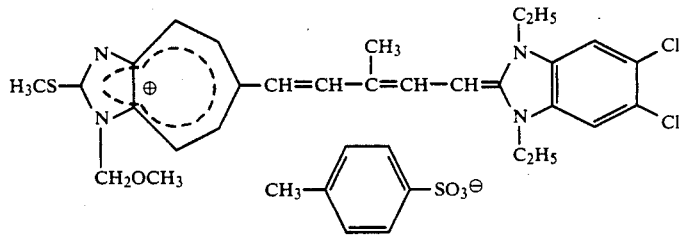
(79)
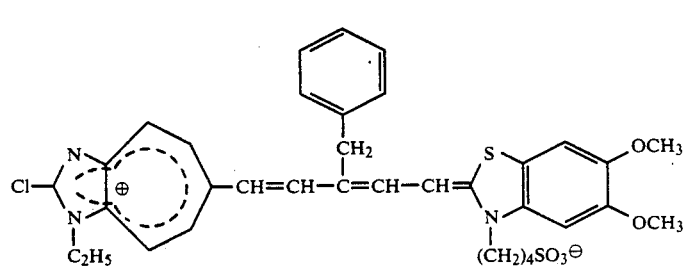

-continued
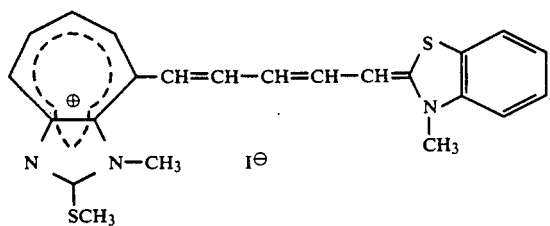 (80)
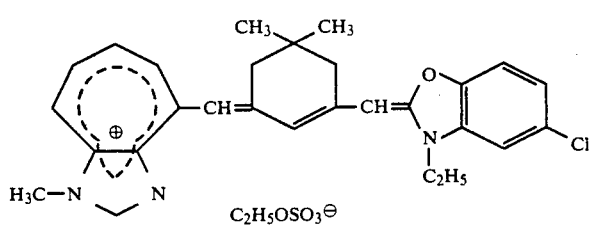 (81)
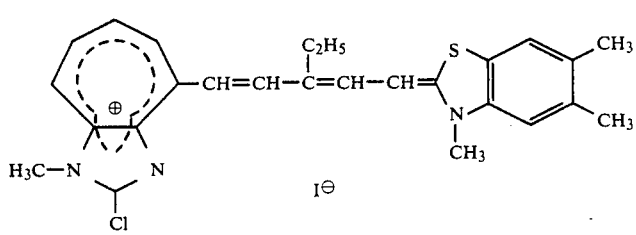 (82)
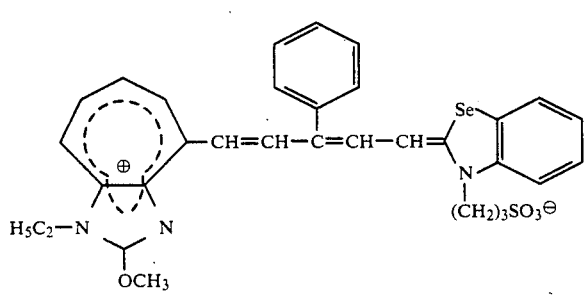 (83)
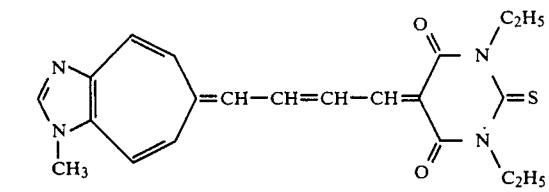 (84)
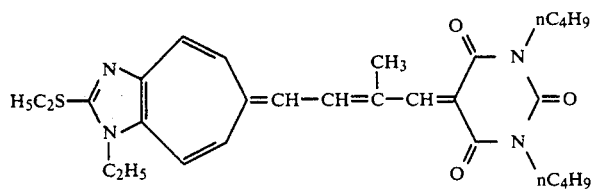 (85)
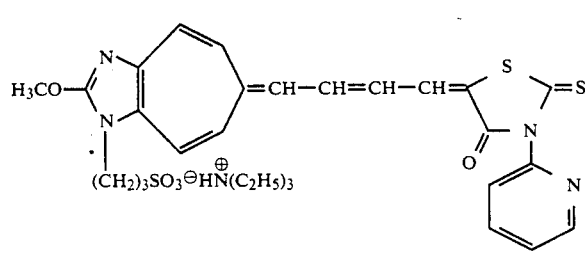 (86)

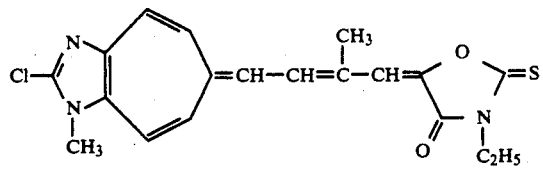
(87)
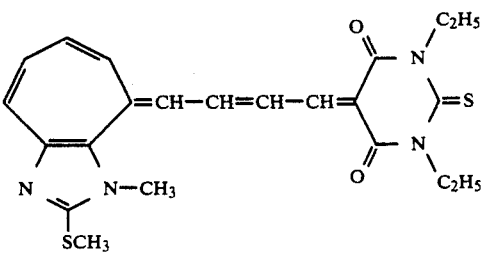
(88)
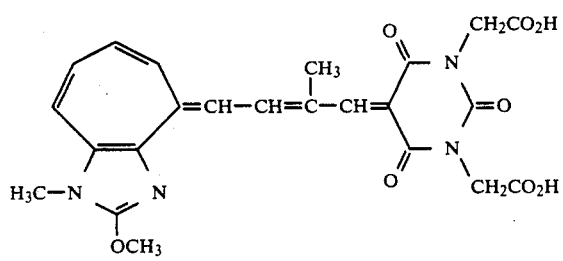
(89)
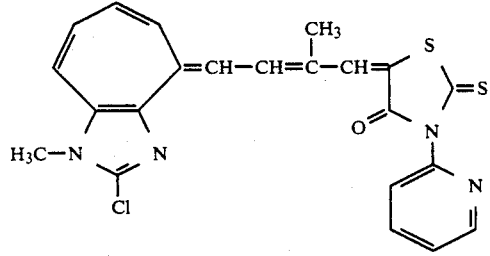
(90)
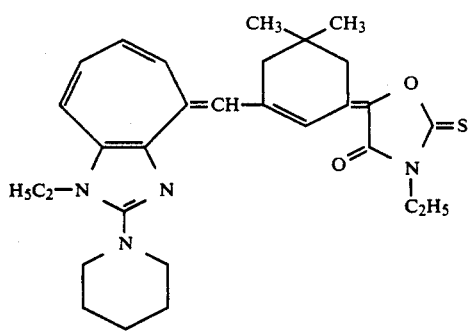
(91)
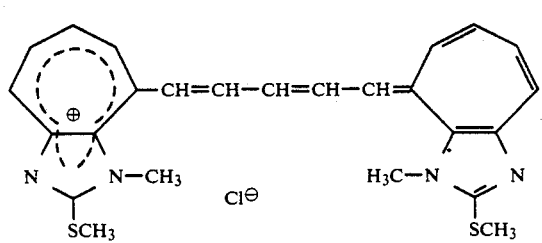
(92)

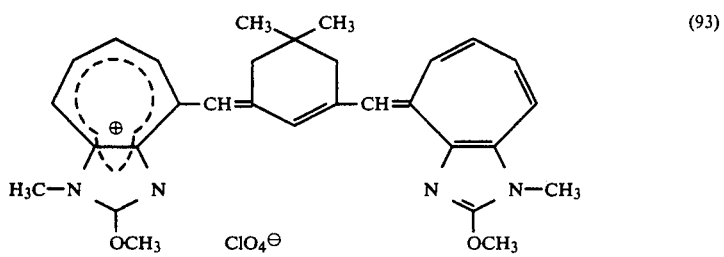
(93)
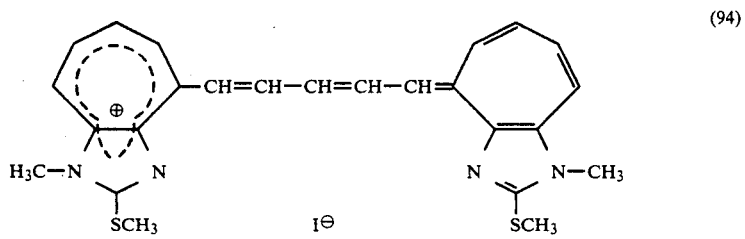
(94)
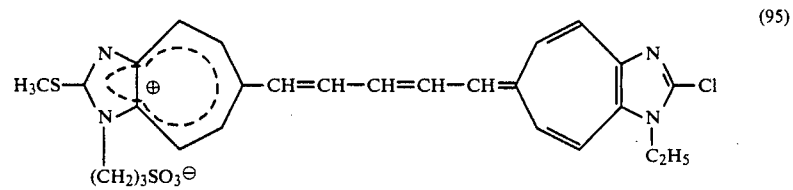
(95)
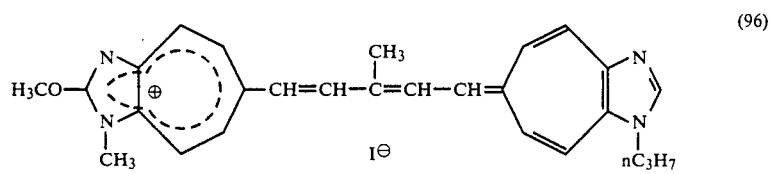
(96)
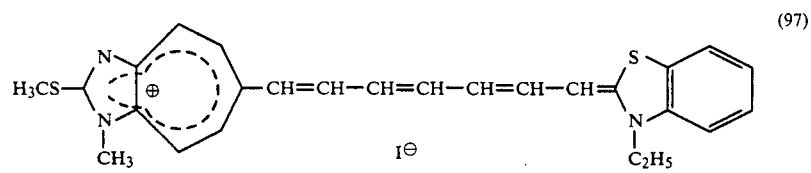
(97)
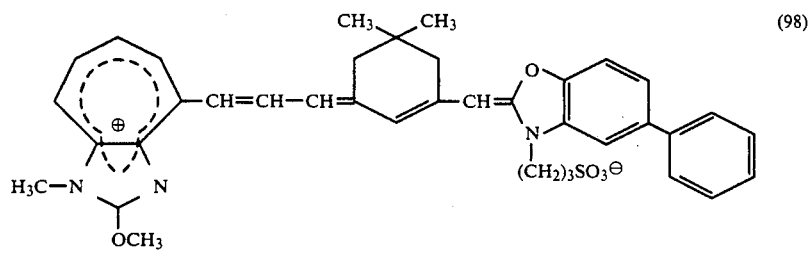
(98)
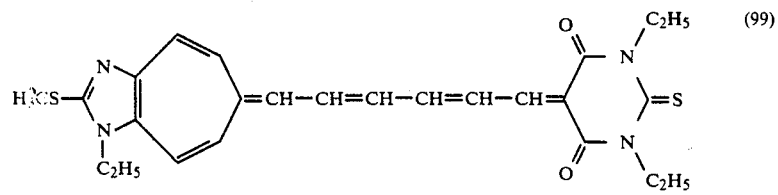
(99)

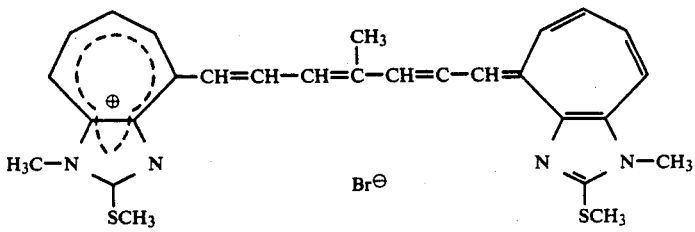
(100)
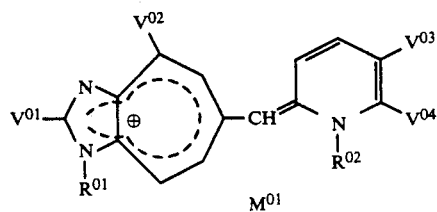
| Compound | V01 | V02 | R01 | R02 | V03 | V04 | M01 |
|---|---|---|---|---|---|---|---|
| (101) | H | H | phenyl | C$_2$H$_5$ | H | H | I$^-$ |
| (102) | SCH$_3$ | H | C$_2$H$_5$ | (CH$_2$)$_4$SO$_3^-$ | Cl | H | — |
| (103) | phenyl | CH$_3$ | nC$_5$H$_{11}$ | CH$_2$CO$_2$H | H | H | Br$^-$ |
| (104) | SCH$_3$ | H | CH$_3$ | C$_2$H$_5$ | (fused benzo) | | I$^-$ |
| (105) | SCH$_3$ | H | CH$_3$ | C$_2$H$_5$ | (fused benzo-OCH$_3$) | | I$^-$ |
| (106) | OCH$_3$ | CH(CH$_3$)$_2$ | (CH$_2$)$_3$SO$_3^-$ | CH$_3$ | (fused benzo-Cl) | | — |
| (107) | phenyl | H | pyridyl | (CH$_2$)$_2$OH | (fused benzo-CH$_3$) | | $^-$O$_3$S-C$_6$H$_4$-CH$_3$ |

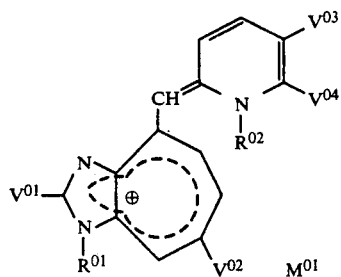
| Compound | $V^{01}$ | $V^{02}$ | $R^{01}$ | $R^{02}$ | $V^{03}$ | $V^{04}$ | $M^{01}$ |
|---|---|---|---|---|---|---|---|
| (108) | H | CH(CH₃)CH₃ | CH₃ | C₂H₅ | H | H | I⁻ |
| (109) | SCH₃ | H | C₂H₅ | (CH₂)₂CO₂H | OCH₃ | H | Br⁻ |
| (110) | SCH₃ | H | CH₃ | C₂H₅ | —(benzo)— | | I⁻ |
| (111) | phenyl | H | tetrahydrofuryl | (CH₂)₃SO₃⁻ | —(benzo)— | | — |
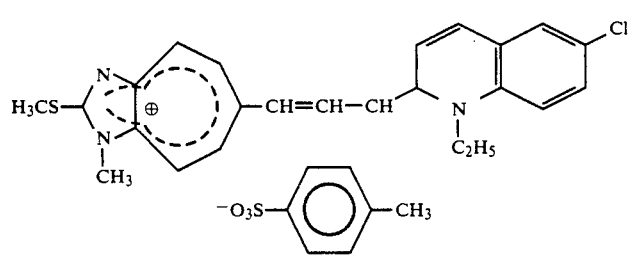
(112)
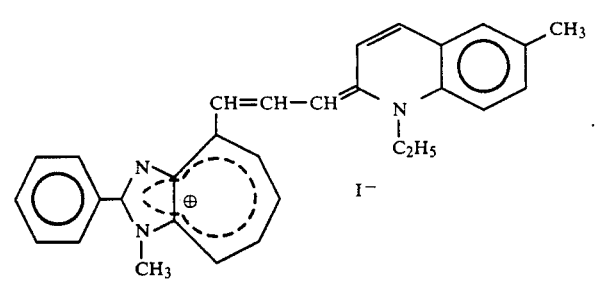
(113)
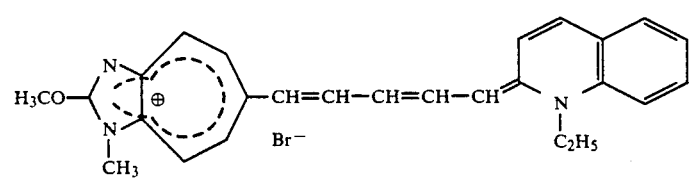
(114)
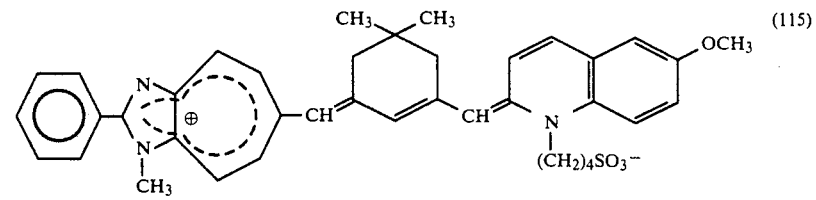
(115)

-continued
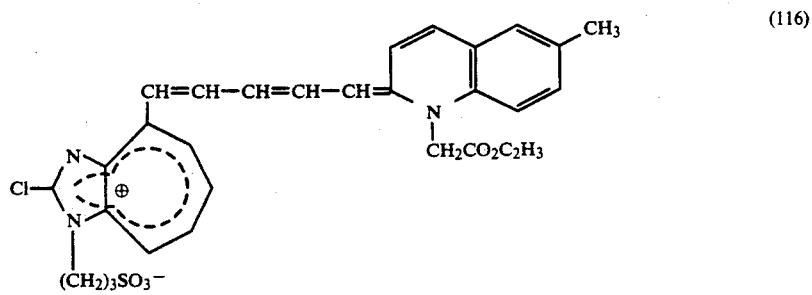
(116)
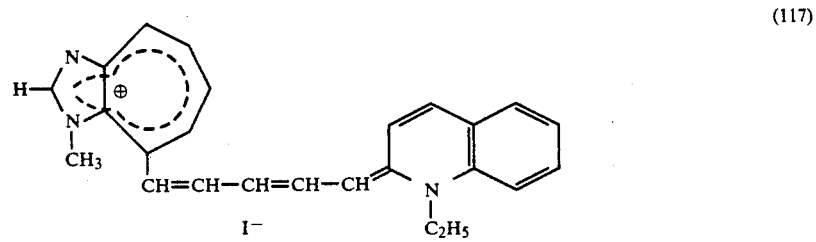
(117)
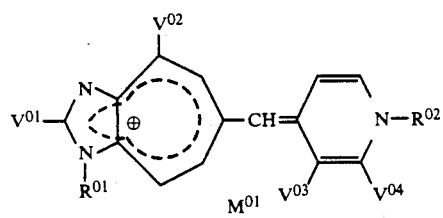
| Compound | V01 | V02 | R01 | R02 | V03 | V04 | M01 |
|---|---|---|---|---|---|---|---|
| (118) | $SCH_3$ | H | $CH_3$ | $C_2H_5$ | H | H | $I^-$ |
| (119) | $SCH_3$ | H | $CH_3$ | $C_2H_5$ | cyclohexene | | $I^-$ |
| (120) | H | H | thiazole | $(CH_2)_4SO_3^-$ | methylcyclohexene | | — |
| (121) | phenyl | $CH_3$ | $CH_2CO_2H$ | $^nC_5H_{11}$ | chlorocyclohexene | | $Br^-$ |

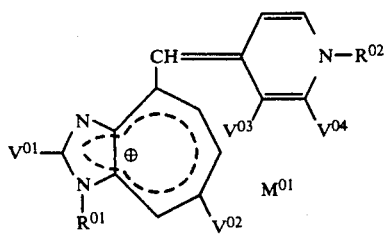
| Compound | V01 | V02 | R01 | R02 | V03 | V04 | M01 |
|---|---|---|---|---|---|---|---|
| (122) | H | CH-CH-CH | C₂H₅ | CH₂OCH₃ | H | H | Cl⁻ |
| (123) | SCH₃ | H | CH₃ | C₂H₅ | (benzo) | | I⁻ |
| (124) | phenyl | H | CH₃ | (CH₂)₃SO₃⁻ | (benzo-CH₃) | | — |
| (125) | OCH₃ | H | imidazolyl | C₂H₅ | (benzo-Cl) | | I⁻ |
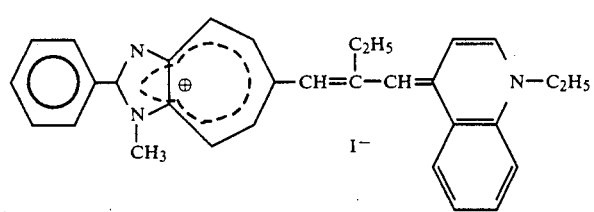
(126)
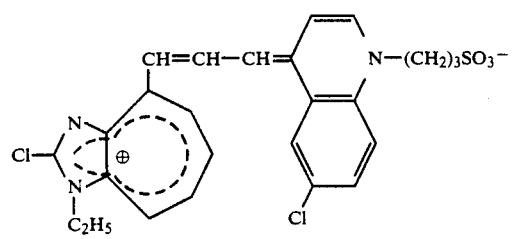
(127)
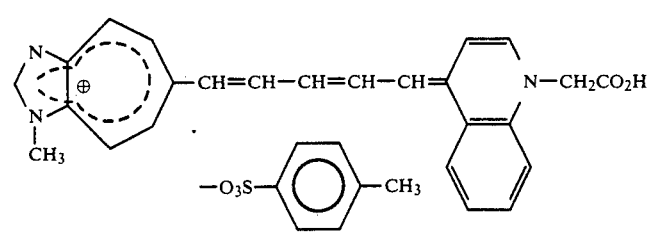
(128)

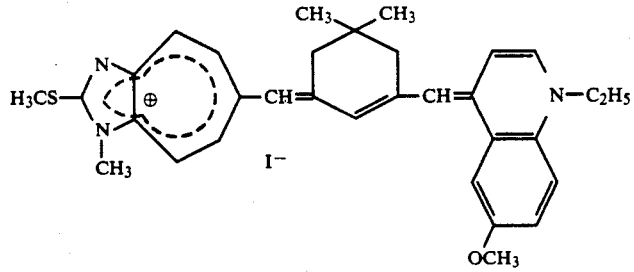
(129)

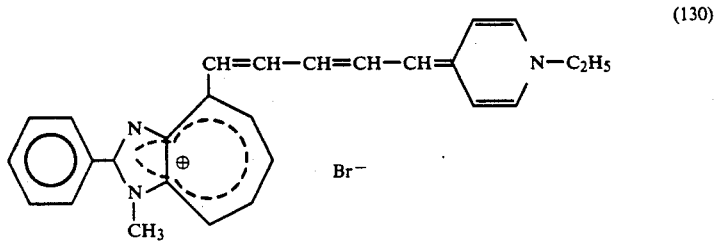
(130)

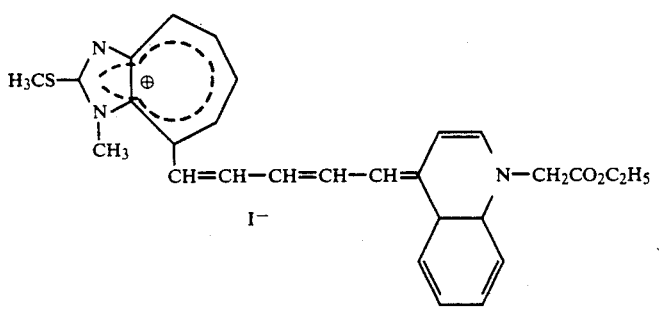
(131)

The following two methods can be employed in the production of the methine dyes of the present invention.

PRODUCTION METHOD NO. 1

A cycloheptimidazolium ion of the general formula (VI) is condensed with a precursor of the general formula (VII) containing an auxochrome and a methine bond, to produce a methine dye of a general formula (VIII) of the present invention.

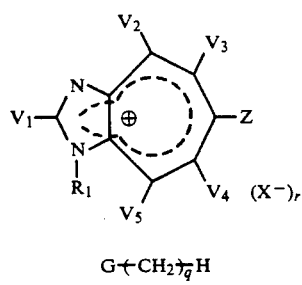
(VI)

G$\pmb{\pm}$CH$_2$$\pmb{\mp}_q$H  (VII)

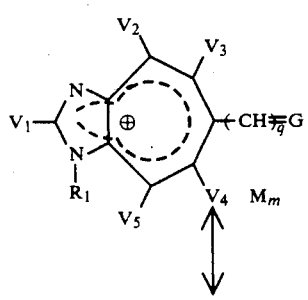
(VIII)

-continued (the continued structure)

In the above formulae, $V_1$ to $V_5$ and $R_1$ have the same meanings as in the formula (I); q represents 0 or 1; and G represents a group of the following formula (IX) or (X):

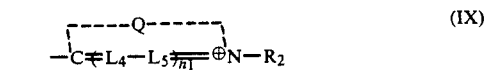
(IX)

(X)

In the formulae (IX) and (X), $R_2$, Q, $L_4$ and $L_5$ have the same meaning as in the formula (II); and D, D', $L_8$ and $L_9$ have the same meanings as in the formula (III).

In the formulae (VI) and (VIII), $R_1$, $V_1$ to $V_5$, M and m have the same meanings as in the formula (I).

In the formula (VI), $X^-$ represents an anion; and r represents 0 or 1; and when the molecule forms an internal salt, r=0.

Examples of the anion residue represented by $X^-$ specifically include inorganic anions and organic anions, and examples of the above-mentioned M can be employed thereas. Preferably, $X^-$ is a trifluoromethanesulfonic acid ion.

In the formula (VI), Z represents a hydrogen atom or a removable group which is generally used in the field of organic synthetic chemistry, for example, including the removable groups described in Jerry March, *Advanced Organic Chemistry, Reactions, Mechanism and Structure* (published by Mcgraw-Hill Kogakusha, 1977, pages 265 to 452). Preferably, the removable group for Z is a halogen atom (e.g., a chlorine atom, a bromine atom, an iodine atom, etc.), an alkylthio group (e.g., an ethylthio group, etc.), an alkoxy group (e.g., a methoxy group, etc.) or an alkylsulfonyl group (e.g., a methylsulfonyl group, etc.).

Especially preferred Z is a hydrogen atom.

In the formulae (VI) and (VIII), the bonding position of Z and the methine group may be of the 4-, 5-, 6-, 7-, and 8-position just as in the formula (I).

In the formula (VII), when G represents a group of the formula (IX) and q is 1, the compound is a methylquaternary compound, and this is a raw material of the corresponding methylene base. The condensation reaction of the base is a well-known technique for production of monomethinecyanine dyes. The reaction is described, for example, in T. H. James, *The Theory of the Photographic Process*, No. 4 (published by Macmillan, 1977, Chapter 8, page 206).

The condensation of methylene bases for production of cyanine dyes requires that each of the two basic nuclei to be reacted contains a reactive substituent, and the cycloheptimidazolium ion of the formula (VI) was found to be able to accept the nucleophilic attack at the ring carbon atoms thereof. Depending on the electron state, the 4-, 6- and 8-positions are highly reactive, and the 4- and 6-positions are more highly reactive. Accordingly, the condensation reaction between the methylene base and the activated cycloheptimidazolium ion can be carried out on the basis of the methylene base condensation reaction in accordance with the conventional techniques which are greatly used in the production of cyanine dyes, for example, by the reaction as described in F. M. Hamer, *Heterocyclic Compounds—Cyanine dyes and related compounds*, Chapters II to XIII, pp. 32–510 (John Wiley & Sons Co., New York, London, 1964).

In the same manner, when q is 0 and G has the formula (X) in the formula (VII), the resulting compound is a ketomethylene or cyanomethylene, and this may be condensed with an activated cycloheptimidazolium ion to produce a dye which is analogous to merocyanine dyes, as described in F. M. Hamer, *Heterocyclic Compounds—Cyanine dyes and related compounds*, Chapter XIV, pp. 511–611 (John Wiley & Sons Co., New York, London, 1964). The reaction position in this reaction is similar to that in the production of the above-mentioned cyanine-analogous dyes. Accordingly, the reaction is preferably effected at the 4-, 6- or 8-position, more preferably at the 4- or 6-position.

The condensation reaction between the ketomethylene or cyanomethylene and the activated cycloheptimidazolium ion can be carried out in accordance with general methods used in the production of merocyanine dyes.

In general, the method to be used for the production of cyanine dyes and merocyanine dyes is the condensation reaction of the compounds of the formulae (VI) and (VII). The condensation reaction can be effected at room temperature or can be accelerated with heating, if desired.

As the reaction solvent, the following solvents may be mentioned: acetonitrile; aliphatic or aromatic hydrocarbons such as benzene, toluene, xylene and decane, as well as halogenated analogues thereof; ethers; pyridine; dimethylsulfoxide; dimethylformamide; and alcohols such as methanol and ethanol, etc.

More preferably, the solvent is acetonitrile, pyridine, dimethylformamide, methanol or ethanol. For a condensation using the methylene based, an organic base can be used, for example, a tertiary amine (e.g., triethylamine, 1,8-diazabicyclo[5,4,0]-7-undecene (DBU), etc.), tetramethylguanidine and piperidine.

The first production method of the present invention is useful for the production of methine dyes in which the cycloheptimidazole nucleus is bonded to the basic nucleus in a form as found in cyanine dyes via one methine group is directly bonded to the acidic nucleus of such form as found in oxonole dyes and merocyanine dyes. Accordingly, the methine dyes obtainable by the first production method are monomethine dyes of the formula (II) and zeromethine dyes of the formula (III).

In addition, by employing the production method as described in F. M. Hamer, *Heterocyclic Compounds—Cyanine Dyes and Related Compounds*, Chapter 2, pages 72 and 73, Chapter 4, page 111 (published by Joh Wiley & Sons, Co., 1964), which is analogous to the above first production method of the present invention, the malonic acid of the formula (VI) and glutaconic acid can be reacted to produce a cycloheptimidazole nucleus-symmetric monomethine or trimethine dye. By the production method, a part of the formula (V) can be produced. In this case, the preferred reaction position of the cycloheptimidazolium ion is the 4- or 6-position, and, more preferably this is the 4-position.

The production of hemicyanine type dyes of the formula (IV), which is a special production method analogous to the first production method, is described hereunder.

The hemicyanine type dye of the formula (IV) can be produced by condensation of a compound of the formula (VI) and a tertiary amine having at least one ethyl group.

In this case, the preferred reaction position is the 4-, 6- or 8-position, and more preferably this is the 4-position.

PRODUCTION METHOD NO. 2

The second production method makes possible the production of methine dyes containing two or more methine groups which connect the cycloheptimidazole nucleus and the remaining basic or acidic nuclei.

Methine dyes obtainable by the second production method are represented by the following formula (XI):

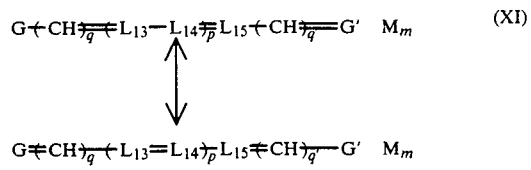

For the production of these dyes, a compound of the general formula (XII):

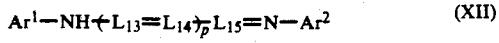

$$Ar^1—NH\!+\!L_{13}\!=\!L_{14}\!\rangle_{\overline{p}}L_{15}\!=\!N—Ar^2 \quad (XII)$$

is first reacted with a compound of the general formula (XIII):

$$G\!+\!CH_2\!\rangle_{\overline{q}}H \quad (XIII)$$

in a condensation reaction, and then the reaction product obtained by the first condensation reaction is further reacted with a compound of the general formula (XIV):

$$G'\!+\!CH_2\!\rangle_{\overline{q'}}—H \quad (XIV)$$

in a further condensation reaction to obtain the intended dye. In the formulae, $Ar^1$ and $Ar^2$ each represents a carbocyclic aromatic group; and G and G' each represents anyone of the groups of the following formula (XV) and the formulae (IX) and (X).

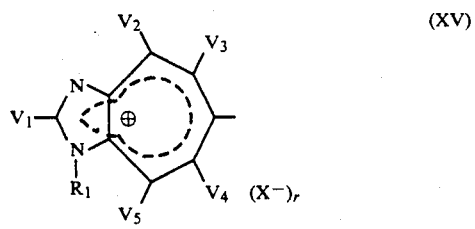

In the formula (XV), $R_1$ and $V_1$ to $V_5$ have the same meanings as in the formula (I); and $X^-$ and r have the same meanings as in the formula (VI).

In the formula (XII) or (XIV), when G or G' satisfies the formula (XV), q is 1. In this case, the bonding position of the methyl group is anyone of the 4-, 5-, 6-, 7- and 8-positions, and this is preferably the 4-, 6- or 8-position, and more preferably the 4- or 6-position.

In the formulae (XI) and (XII), $L_{13}$, $L_{14}$ and $L_{15}$ each represents an optionally substituted methine group, which has the same meaning as $L_1$, $L_2$, $L_3$, $L_4$ and $L_5$ in the formula (II).

q and q' each is 0 or 1; and when G or G' is the group of the formula (IX) or (XV), q is 1, and when G or G' is the group of the formula (X), q is 0.

p represents 0 or a positive integer, and is typically 0, 1, 2 or 3.

At least one of G and G' represents the group of the formula (XV).

As is apparent from the above explanation, the indispensable starting material for the second production method is a cycloheptimidazolium ion having a methyl-substituent.

In the case of the production of methine dyes with only one cycloheptimidazole nucleus, the compound of the formula (XIII) or (XIV) in which one of G and G' represents the group of the formula (IX) or (X) is used.

The compound which is necessary as the other starting compound is one represented by the formula (XII). When p is O and $L_{15}$ is —CH—, the compound of the formula (XII) is a diarylformamidine, and typically diphenylformamidine. When p is a positive integer, the compound of the formula (XII) to be obtained is an analogue of a diarylformamidine vinylog.

When the diarylformamidine of the formula (XII) or the vinylog analogue thereof is reacted with the compound of the formula (XIII) where G is one of the formulae (IX) and (X), the compound obtained is an intermediate generally used for the production of cyanine dyes and merocyanine dyes.

Although the intermediate is often directly used, the reactivity thereof can be increased by acyl-substitution of the N-hydrogen atom, for example, by reaction with a carboxylic acid or its anhydride. The acetyl-substituted intermediate is most generally used. When the intermediate contains the quaternary ammonium nucleus as represented by the formula (IX), the intermediate obtained is often designated as I.C.I. intermediate, while if the intermediate contains the ketomethylene or cyanomethylene group as represented by the formula (X), the intermediate obtained is often designated as a Dains intermediate. The method for the use of the I.C.I. intermediate and the Dains intermediate in the production of cyanine dyes and merocyanine dyes is described in T. H. James, *The Theory of the Photographic Process*, pages 195 to 210, supra.

When the diarylformamidine of the formula (XII) or the vinylog analogue thereof is reacted with a compound of the formula (XIII) in which G has the formula (XV), a new intermediate usable for the production of dyes can be obtained. The thus-obtained cycloheptimidazole nucleus-containing dye intermediate can be used in the same manner as the I.C.I. intermediate and the Dains intermediate which are known in the production of methine dyes.

The dye intermediate obtained by the reaction of the compounds of the formula (XII) and the formula (XIII), which is optionally acylated, can be represented by the following formula (XVI):

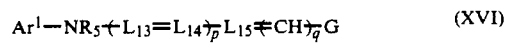

$$Ar^1—NR_5\!+\!L_{13}\!=\!L_{14}\!\rangle_{\overline{p}}L_{15}\!\mp\!CH\!\rangle_{\overline{q}}G \quad (XVI)$$

in which $R_5$ represents a hydrogen atom or an acyl group; and the other symbols have the same meanings as defined above.

For the production of the dyes of the formula (XI), a compound of formula (XIV) may be reacted with a dye intermediate of the formula (XVI) by a condensation reaction, as described in F. M. Hamer, *Heterocyclic Compounds—Cyanine dyes and related compounds*, Chapters II to XIV, pp. 32-611 (John Wiley & Sons, Co., New York, London, 1964). Except for the methyl-substituted cycloheptimidazolium ion, the reaction order from the starting material to the final dye is the same as the production method which is known for the production of cyanine dyes and merocyanine dyes. Although the reaction generally proceeds at room temperature, this can be accelerated under heating, if desired. The reaction can be carried out in the same solvent as used in the abovementioned first production method.

The second production method is more advantageous than the first method in that more methine groups can be introduced into the dyes and the substituent position of the methine bond of the cycloheptimidazole nucleus is not free but is specific so that the formation of by-products is small. In accordance with the second production method, the desired number of the substituted or unsubstituted methine groups can be introduced into the dyes.

In practice, the absorption of the dye having one or more cycloheptimidazole nuclei is often shifted to a dark color, and therefore, the number of p in the formula (XI) rarely needs to exceed 3 so as to obtain the absorption of the dye of a long wavelength.

As the methine source, the diarylformamidine of the formula (XII) and the vinylog analogue thereof are illustrated herein, but needless to say, other methine sources such as orthoesters or vinylog analogues thereof can of course be used in the present invention.

Using the second production method, the methine dyes of the formulae (II), (III) and (V) can be produced.

The production of the cycloheptimidazolium ion compound to satisfy the formula (VI) or (XV), which is a starting compound in the first and second production methods, is explained hereunder, regarding one typical example in which:

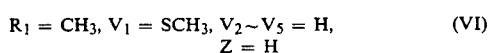  (VI)

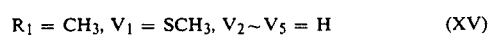  (XV)

When 2-hydroxy-2,4,6-cycloheptatrien-1-one, which can easily be obtained by the method described in *Journal of the American Chemical Society*, Vol. 87, No. 22, pages 5257 to 5259 (1965), or 2-hydroxy-5-methyl-2,4,6-cycloheptatrien-1-one, which can easily be obtained by the method described in *Bulletin of the Chemical Society of Japan*, Vol. 32, pages 493 to 496 (1959), is methylated with a methylating agent (e.g., dimethylsulfuric acid), 2-methoxy-2,4,6-cycloheptatrien-1-one or 2-methoxy-5-methyl-2,4,6-cycloheptatrien-1-one can be obtained. Next, each of them is condensed with thiourea, to obtain 2-mercaptocycloheptimidazole or 2-mercapto-6-methylcycloheptimidazole, respectively. After further S-methylation with a methylating agent (e.g., methyl iodide), 2-methylthiocycloheptimidazole or 6-methyl-2-methylthiocycloheptimidazole can be obtained. After even further N-methylation with a methylating agent (e.g., methyl trifluoromethanesulfonate), 3-methyl-2-methylthiocycloheptimidazolium ion or 3,6-dimethyl-2-methylthiocycloheptimidazolium ion can be obtained.

The above reaction is summarized in the following reaction scheme:

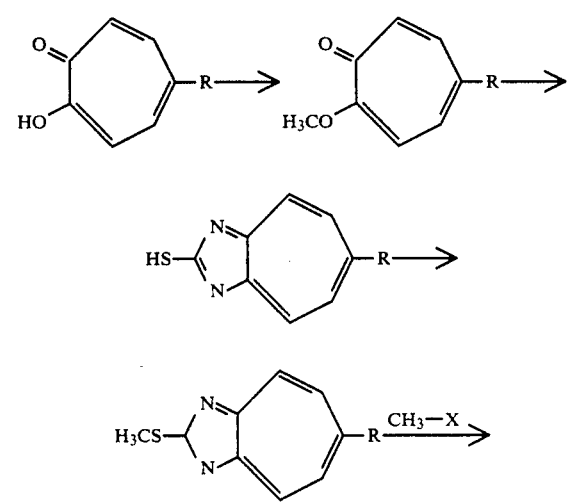

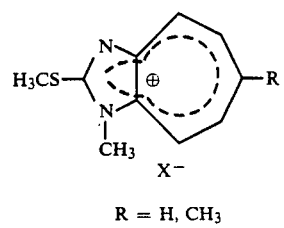

$R = H, CH_3$

Further, in the case that in the formulae (VI) and (XV), $R_1$ represents an aryl group or a heterocyclic group, the reaction is summarized in the following reaction scheme:

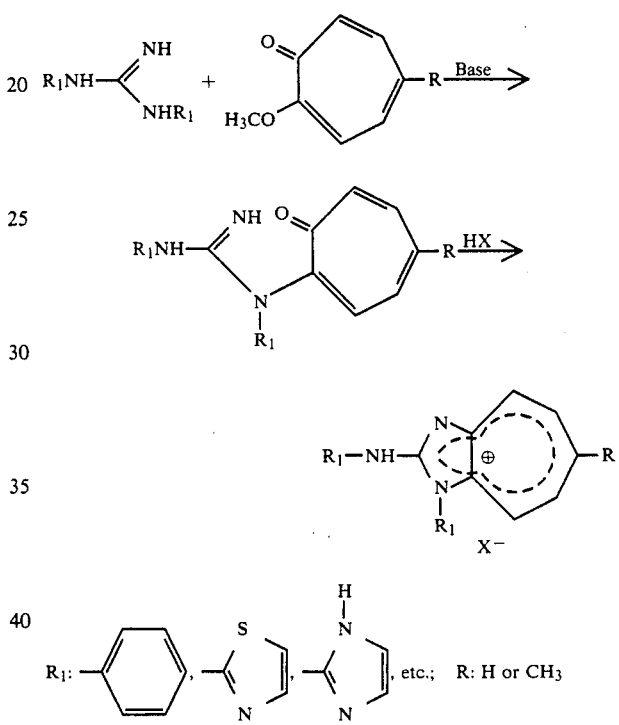

That is, the reaction proceeds first by treatment with a base (such as triethylamine, DBU) and then with an acid (such as hydrochloric acid) to thereby cause a cyclization to occur.

The following examples are given to illustrate the present invention in further detail but not to limit it in any way. Unless otherwise indicated herein, all parts, percents, ratios and the like are by weight.

EXAMPLE 1

Production of Dye (7)

The production of Dye (7) is explained below in order from the preparation of the raw materials.

(a) Production of 2-Methoxy-2,4,6-cycloheptatrien-1-one 200 g of 2-hydroxy-2,4,6-cycloheptatrien-1-one, easily obtained by the method described in *Journal of the American Chemical Society*, Vol. 87, No. 22, pages 5257 to 5259 (1965), and 340 g of potassium carbonate were added to 1.3 liters of 10% aqueous acetone, and 310 g of dimethylsulfuric acid was added thereto and heated under reflux for 8 hours. After leaving such overnight, the inorganic substance precipitated was separated by filtration, and the acetone in the filtrate was evaporated off under reduced pressure. One liter of water was added to the concentrated filtrate, and this was extracted with chloroform (0.3 liter×3). Next, the chloroform solution was dried with anhydrous sodium sulfate and, after the solvent was evaporated off, this was distilled under reduced pressure (120° C./0.5 mmHg). 205.7 g of a colorless liquid was obtained. Yield: 92.3%.

(b) Productin of 2-Mercaptocycloheptimidazole

In accordance with the method described in *Journal of the Americal Chemical Society*, Vol. 76, pages 3352 to 3353 (1954), 150 g of 2-methoxy-2,4,6-cycloheptatrien-1-one and 84 g of thiourea were added to 255 g of 28% sodium methoxide/methanol solution and stirred for 30 minutes at room temperature. Further, 600 ml of methanol was added and acetic acid was added until the pH of the resulting solution became 5 or so. The crystals precipitated were separated by filtration and washed with methanol. Next, the thus obtained crystals were added to one liter of methanol and heated under reflux for 30 minutes. After cooling to room temperature, the crystals were separated by filtration and then dried. 125 g of yellow crystals was obtained.

Yield: 70.0%. m.p.: 300° C. or higher.

(c) Production of 2-Methylthiocycloheptimidazole 38 g of potassium hydroxide was dissolved in 800 ml of methanol and then 100 g of 2-mercaptocycloheptimidazole was added thereto and stirred under heating at an internal temperature of about 45° C. Next, 131.2 g of dimethylsulfuric acid was dropwise added and further stirred under heating at an internal temperature of about 45° C. for 1 hour. After the solvent was evaporated off to some degree under reduced pressure, one liter of water was added, and the resulting solution was extracted with chloroform (0.5 liter×2). Then, the chloroform layer was dried with anhydrous sodium sulfate, and the solvent was evaporated off under reduced pressure until the chloroform solution became 200 ml. Next, one liter of hexane was added to the thus concentrated solution whereby a precipitate crystallized out. This was separated by filtration and dried. 89 g of colorless crystals was obtained.

Yield: 82.0%. m.p.: 101° to 102° C.

(d) Production of 3-Methyl-2-methylthiocycloheptimidazolium trifluoromethanesulfonate 25 g of 2-methylthiocycloheptimidazole was added to 100 ml of anisole and stirred under cooling with ice. Next, 28 g of methyl trifluoromethanesulfonate was dropwise added and stirred under cooling with ice. Further, everything was stirred for 2 hours and 30 minutes at room temperature, and then, 200 ml of ethyl acetate was added, and the crystals precipitated were separated by filtration and dried. 39.7 g of a colorless crystals was obtained.

Yield: 82.0%. m.p.: 163° to 164° C.

(e) Production of Dye (7)

2.8 g of 3-methyl-2-methylthiocycloheptimidazolium trifluoromethanesulfonate and 2.3 g of 3-ethyl-2-methylbenzothiazolium p-toluenesulfonate were added to 50 ml of acetonitrile and, after 2.3 ml of triethylamine was added, everything was heated under reflux for 1 hour. Next, after the solvent was evaporated off under reduced pressure, the reaction product was purified by silica gel column chromatography with a developer of a mixed solvent of methanol/chloroform (=¼ by volume). The crystals obtained was added to 50 ml of methanol and dissolved under heating, and then, the insoluble material was filtered off while hot. A methanol solution (5 ml) containing 1.2 g of sodium iodide was added to the resulting filtrate and then allowed to cool. The crystals precipitated were separated by filtration and then washed with water and dried. 0.75 g of a violet crystals was obtained.

Yield: 24%. m.p.: 260° to 264° C.

$\lambda_{max}=574$ nm ($\epsilon=9.95\times10^{-4}$) (methanol solvent).

During the production of Dye (7) as above, slight amounts of Dye (26) in which the cycloheptimidazole nucleus is substituted in the 4-position and Dye (25) in which the nucleus is substituted in the 8-position were obtained as by-product dyes. Also in the following examples, the same by-product dyes were obtained, when the dyes were produced in accordance with the first production method (Examples 2, 3, 4, 5, 6, 7, 8, 9 and 10).

EXAMPLE 2

Production of Dye (14)

4 g of 3-methyl-2-methylthiocycloheptimidazolium trifluoromethanesulfonate, as obtained in Example 1-(d), and 3.53 g of 3-ethyl-2-methylbenzoxazolium p-toluenesulfonate were added to 50 ml of acetonitrile, and 3 ml of triethylamine was further added, and then everything was heated under reflux for one hour. 200 ml of ethyl acetate was added to the reaction solution, and the crystals precipitated were separated by filtration. The resulting crystals were added to 100 ml of methanol and dissolved under heating, and then the insoluble substance was filtered off while hot. A methanol solution (5 ml) containing 1.5 g of sodium iodide was added to the resulting filtrate and then such was allowed to cool. The crystals precipitated were separated by filtration and washed with methanol and water and then dried. 1.8 g of violet crystals were obtained.

Yield: 36%. m.p.: 300° C. or higher.

$\lambda_{max}=547$ nm ($\epsilon=1.05\times10^5$) (methanol solvent).

EXAMPLE 3

Production of Dye (30)

3 g of 3-methyl-2-methylthiocycloheptimidazolium trifluoromethanesulfonate, as obtained in Example 1-(d), and 1.77 g of N,N-diethylthiobarbituric acid were added to 30 ml of pyridine and stirred under heating at an internal temperature of 50° C. for 30 minutes. 200 ml of ethyl acetate was added to the reaction solution, and the crystals precipitated were separated by filtration. The crystals were added to a mixed solvent of methanol (100 ml)/chloroform (200 ml) and dissolved by heating under reflux, and then the insoluble substance was filtered out while hot. The resulting filtrate was further distilled under reduced pressure until the amount of the solvent became 120 ml. After standing at room temperature, the crystals formed were separated by filtration and washed with methanol and then dried. One g of red crystals were obtained.

Yield: 29.2%. m.p.: 300° C. or higher.

$\lambda_{max}=530$ nm ($\epsilon=5.18\times10^4$) (methanol solvent).

EXAMPLE 4

Production of Dye (31)

3 g of 3-methyl-2-methylthiocycloheptimidazolium trifluoromethanesulfonate, as obtained in Example 1-(d), and 2.1 g of N,N-di-n-butylbarbituric acid were added to 30 ml of pyridine and stirred under heating at an internal temperature of 50° C. for 1 hour. 200 ml of water was added to the reaction solution, and the crystals precipitated were separated by filtration. The crystals were added to a mixed solvent of isopropanol (100 ml)/chloroform (100 ml) and dissolved therein, and then the insoluble substance was filtered out. Next, the resulting filtrate was further distilled under reduced pressure until the amount of the solvent became 100 ml. After standing at room temperature, the crystals formed were separated by filtration and washed with isopropanol and then dried. 1.06 g of a red crystal was obtained.

Yield: 28.0%. m.p.: 219° to 221° C.

$\lambda_{max}=516$ nm ($\epsilon=4.59\times 10^4$) (methanol solvent).

EXAMPLE 5

Production of Dye (39)

5 g of 3-methyl-2-methylthiocycloheptimidazolium trifluoromethanesulfonate, as obtained in Example 1-(d), and 0.84 g of malonic acid were added to 50 ml of pyridine and heated under reflux for 30 minutes. 200 ml of water was added to the reaction solution, and 2.2 g of sodium iodide was added. The crystals precipitated were separated by filtration, and this was purified by silica gel column chromatography with a developer of a mixed solvent of methanol/chloroform (=1/1 by volume). The crystals thus obtained were added to a mixed solvent of methanol (50 ml)/chloroform (50 ml) and dissolved therein, and after the insoluble substance was filtered out, the resulting filtrate was further distilled until the amount of the solvent became 60 ml, and then this was allowed to cool. The crystals precipitated were separated by filtration and washed with methanol and then dried. 1.1 g of violet crystals were obtained.

Yield: 14.4%. m.p.: 300° C. or higher.

$\lambda_{max}=674$ nm ($\epsilon=6.49\times 10^4$) (methanol solvent).

Also during the production of Dye (39) as above, slight amounts of Dye (42) in which the cycloheptimidazole nucleus is substituted in the 6-position and Dye (38) in which the nucleus is substituted in the 8-position were obtained as by-product dyes. The following Example 6 was quite same in this respect.

EXAMPLE 6

Production of Dye (68)

10 g of 3-methyl-2-methylthiocycloheptimidazolium trifluoromethanesulfonate, as obtained in Example 1-(d), and 3.82 g of glutaconic acid were added to 50 ml of pyridine and stirred under heating at an internal temperature of 50° C. for 1 hour. 200 ml of ethyl acetate was added to the reaction solution and the crystals precipitated were separated by filtration. The crystals were dissolved in one liter of methanol by heating under reflux, and after the insoluble substance was filtered out while hot, a methanol solution (50 ml) containing 1 g of sodium iodide was added to the resulting filtrate. Next, the solvent was evaporated off to 200 ml. The crystal precipitated was separated by filtration, washed with methanol and water and then dried. 2 g of dark violet crystals were obtained.

Yield: 12.5%. m.p.: about 200° C. (decomposition).

$\lambda_{max}=774$ nm ($\epsilon=1.14\times 10^{-5}$) (methanol solvent).

EXAMPLE 7

Production of Dye (1)

3 g of 3-methyl-2-methylthiocycloheptimidazolium trifluoromethanesulfonate, as obtained in Example 1-(d), was added to 30 ml of acetonitrile, and 1.5 ml of triethylamine was added and stirred under heating at an internal temperature of 60° C. for 1 hour. After the reaction, the solvent was evaporated off and the crystals formed were purified by silica gel column chromatography with a developer of a mixed solvent of methanol/chloroform (=¼ by volume). The crystal thus obtained was dissolved in 10 ml of methanol and a methanol solution (3 ml) containing 0.7 g of sodium iodide was added thereto. Next, 100 ml of water was added and the crystals precipitated were separated by filtration, washed with methanol and dried. 0.5 g of red crystals were obtained.

Yield: 13.7%. m.p.: 219° to 221° C.

$\lambda_{max}=522$ nm ($\epsilon=8.12\times 10^4$) (methanol solvent).

EXAMPLE 8

Production of Dye (9)

The production of Dye (9) is explained below in order from the preparation of the raw materials.

(a) Production of 2-Methoxycycloheptimidazole

In accordance with the method described in *Bulletin of the Chemical Society of Japan*, Vol. 33, No. 1, pages 56 to 58 (1960), 3 g of 2-methylthiocycloheptimiazole, as obtained in Example 1-(c) was added to 50 ml of methanol, and 1 g of sodium methoxide was added thereto. After heating under reflux for 10 hours, the solvent was evaporated off. Next, 50 ml of benzene was added and the insoluble substance was filtered out, and then the filtrate was concentrated. The thus obtained crystals were purified by silica gel column chromatography with a developer solvent of ethyl acetate. 1 g of colorless crystals were obtained.

Yield: 36.8%. m.p.: 94° C.

(b) Production of 2-Methoxy-3-methylcycloheptimidazolium trifluoromethanesulfonate 0.9 g of 2-methoxycycloheptimiazole was added to 5 ml of anisole, and 1.1 g of methyl trifluoromethanesulfonate was dropwise added thereto. After stirring for 1 hour at room temperature, 30 ml of ethyl acetate was added, and the crystals precipitated were separated by filtration and then dried. 1.1 g of colorless crystals was obtained.

Yield: 60.4%. m.p.: 132° to 124° C.

(c) Production of Dye (9)

1 g of 2-methoxy-3-methylcycloheptimidazolium trifluoromethanesulfonate and 1.08 g of 3-ethyl-2-methylbenzothiazolium p-toluenesulfonate were added to 30 ml of acetonitrile, and 0.96 ml of triethylamine was added thereto and heated under reflux for 40 minutes. After the solvent was evaporated off, the reaction product was purified by silica gel column chromatography with a developer of a mixed solvent of methanol/chloroform (=¼ by volume).

The crystals obtained were dissolved in 50 m of methanol, and after the insoluble substance was filtered out while hot, a methanol solution (5 ml) containing 0.5 g of sodium iodide was added. The crystals precipitated were separated by filtration, washed with methanol and water and then dried. 0.2 g of red crystals were obtained.

Yield: 13.9%. m.p.: 190° to 191° C.

$\lambda_{max}=557$ nm ($\epsilon=1.04\times10^5$) (methanol solvent).

EXAMPLE 9

Production of Dye (8)

The production of Dye (8) is explained below in order from the preparation of the raw materials.

(a) Production of 2-Hydroxycycloheptimidazole

In accordance with the method described in *Journal of the Americal Chemical Society*, Vol. 76, pages 3352 to 3353 (1954), 60 g of 2-methylthiocycloheptimidazole, as obtained in Example 1-(c), was added to 300 ml of concentrated hydrochloric acid (hydrogen chloride content: 35%) and heated under reflux for 2 hours and 30 minutes. Next, 500 ml of ethanol was added and everything was stirred at room temperature, and then the crystals precipitated were separated by filtration. The crystals thus obtained were dissolved in 0.5 liter of water, and sodium hydrogencarbonate was added to adjust the pH thereof to about pH 7 or so. The crystals precipitated were separated by filtration, washed with water and then dried. 40 g of pale yellow crystals were obtained.

Yield: 80.3%. m.p.: 245° C.

(b) Production of 2-chlorocycloheptimidazole

In accordance with the method described in *Chemical and Pharmaceutical Bulletin*, Vol. 16, No. 7, pages 1300 to 1307 (1968), 10 g of 2-hydroxycycloheptimidazole, 150 g of phosphorus oxychloride and 12 g of N,N-diethylaniline were stirred under heating at an internal temperature of 70° C. for 6 hours and 30 minutes. After the reaction, the phosphorus oxychloride was evaporated off under reduced pressure, and the resulting reaction mixture was poured into 500 ml of ice-water. Sodium hydrogencarbonate was added to the resulting solution until the pH thereof became neutral, and this was extracted with chloroform (250 ml×2). The chloroform layer was dried with anhydrous sodium sulfate and the solvent was evaporated off, and then the reaction product was purified by silica gel column chromatography with a developer solvent of ethyl acetate. 2.7 g of colorless crystals were obtained.

Yield: 24%. m.p.: 162° to 163° C.

(c) Production of 2-Chloro-3-methylcycloheptimidazolium trifluoromethanesulfonate 0.78 g of 2-chlorocycloheptimidazole was added to 4 ml of anisole, and 0.93 mg of methyl trifluoromethanesulfonate was dropwise added thereto and everything was stirred for 40 minutes at room temperature.

50 ml of ethyl acetate was added to the reaction solution, and the crystals precipitated were separated by filtration and dried.

1.27 g of colorless crystals were obtained.

Yield: 81.5%. m.p.: 109° to 110° C.

(d) Production of Dye (8)

1.2 g of 2-chloro-3-methylcycloheptimidazolium trifluoromethanesulfonate and 1.28 g of 3-ethyl-2-methylbenzothiazolium p-toluenesulfonate were added to 30 ml of acetonitrile, and 1 ml of triethylamine was added thereto and heated under reflux for 1 hour and 30 minutes. After the reaction, the solvent was evaporated off, and then the reaction product was purified by silica gel column chromatography with a developer of a mixed solvent of methanol/chloroform (=¼ by volume). The crystals obtained were dissolved in 100 ml of methanol, and the insoluble substance was filtered out, and then a methanol solution (5 ml) containing 0.6 g of sodium iodide was added to the resulting filtrate. After this was left at room temperature for a while, the crystals precipitated were separated by filtration and washed with a small amount of methanol and then dried.

100 mg of red crystals were obtained.

Yield: 5.7%. m.p.: about 120° C. (decomposition).

$\lambda_{max}=552$ nm ($\epsilon=4.32\times10^4$) (methanol solvent).

EXAMPLE 10

Production of Dye (6)

The production of Dye (6) is explained below in order from the preparation of the raw materials.

(a) Production of Cycloheptimidazole

In accordance with the method described in *Journal of the Americal Chemical Society*, Vol. 76, pages 3352 and 3353 (1954), 23 g of 2-mercaptocycloheptimidazole, as obtained in Example 1-(b), was added to 210 ml of 10% nitric acid and everything was stirred under heating at an internal temperature of from 80° to 90° C. for 1 hour. Sodium hydrogencarbonate was added to the reaction solution so as to neutralize the solution, and this was extracted with chloroform (250 ml×2). The chloroform layer was dried with anhydrous sodium sulfate, and then the solvent was evaporated off until the amount of the chloroform solution became 50 ml. Next, 200 ml of hexane was added thereto. The crystals precipitated were separated by filtration and dried.

7 g of pale yellow crystals were obtained.

Yield: 38.5%. m.p.: 120° C.

(b) Production of Dye (6)

3.8 g of cycloheptimidazole was added to 20 ml of anisole, and 7.2 g of methyl trifluoromethanesulfonate was dropwise added thereto and stirred for 30 minutes at room temperature. The oily product precipitated was removed by decantation, and the oily product and 5.1 g of 3-ethyl-2-methylbenzothiazolium p-toluenesulfonate were added to 50 ml of acetonitrile, and then 4 ml of triethylamine was added thereto. After heating under reflux for 1 hour, the solvent was evaporated off. The crude product thus obtained was purified twice by silica gel column chromatography with a developer of a mixed solvent of methanol/chloroform (=¼ by volume). 50 ml of methanol was added to the crystals obtained and they were dissolved. A methanol solution (5 ml) containing 1.5 g of sodium iodide was added to the resulting solution. After standing for a while, the crystals precipitated were separated by filtration, washed with methanol and dried.

0.5 g of a red crystal was obtained.

Yield: 3.8%. m.p.: 288° to 290° C.

$\lambda_{max}=550$ nm ($\epsilon=5.98\times10^4$) (methanol solvent).

EXAMPLE 11

Production of Dye (7): Alternative to Example 1

The production of Dye (7) is explained below in order from the preparation of the raw materials.

(a) Production of
2-Methoxy-5-methyl-2,4,6-cycloheptatrien-1-one 223 g of 2-hydroxy-5-methyl-2,4,6-cycloheptatrien-1-one, as obtained by the method described in *Bulletin of the Chemical Society of Japan*, Vol. 32, pages 493 to 496 (1959), and 340 g of potassium carbonate were added to 1.3 liters of 10% aqueous acetone, and 310 g of dimethylsulfuric acid was added thereto and everything was heated under reflux for 7 hours. After standing overnight, the inorganic substance precipitated was separated by filtration, and the acetone in the resulting filtrate was evaporated off under reduced pressure. One liter of water was added to the thus concentrated filtrate solution, and then this was extracted with chloroform (0.25 liter×4). Next, the chloroform layer was dried with anhydrous sodium sulfate and, after the solvent was evaporated off, this was distilled under reduced pressure (130° C./0.5 mmHg).

224 g of a colorless liquid was obtained.
Yield: 91%.

(b) Production of
2-Mercapto-6-methylcycloheptimidazole 165 g of 2-methoxy-5-methyl-2,4,6-cycloheptatrien-1-one and 84 g of thiourea were added to 255 g of 28% sodium methoxide/methanol solution and everything was stirred for 30 minutes at room temperature. Next, 60 ml of methanol was added, and then acetic acid was added until the pH value of the resulting solution became 5 or so. The crystals thus precipitated were separated by filtration, fully washed with methanol and then dried.

145.4 g of yellow crystals were obtained.
Yield: 75%. m.p.: 300° C. or higher.

(c) Production of
6-Methyl-2-methylthiocycloheptimidazole 38 g of potassium hydroxide was dissolved in 800 ml of methanol, and 108.5 g of 2-mercapto-6-methylcycloheptimidazole was added thereto and everything was stirred under heating at an internal temperature of about 45° C. Next, 131.2 g of dimethylsulfuric acid was dropwise added and everything was further stirred under heating at an internal temperature of about 45° C. for 1 hour. After the solvent was evaporated off to some extent under reduced pressure, 1 liter of water was added and the resulting solution was extracted with chloroform (0.5 liter×2). The chloroform layer was dried with anhydrous sodium sulfate, and then the solvent was evaporated off under reduced pressure until the chloroform solution became 200 ml. To this was added one liter of hexane, whereby crystals precipitated out. The thus formed crystals were separated by filtration and dried.

99.6 g of colorless crystals were obtained.
Yield: 85.0%. m.p.: 110° to 111° C.

(d) Production of
3,6-dimethyl-2-methylthiocycloheptimidazolium trifluoromethanesulfonate 27 g of 6-methyl-2-methylthiocycloheptimidazole was added to 100 ml of anisole and stirred under cooling with ice. Next, 28 g of methyl trifluoromethanesulfonate was dropwise added and further everything was stirred under cooling with ice. After everything was stirred for 1 hour at room temperature, 200 ml of ethyl acetate was added, and the crystals precipitated were separated by filtration and dried.

40.3 g of colorless crystals were obtained.
Yield: 80%. m.p.: 175° to 177° C.

(e) Production of Dye (7)

3 g of 3,6-dimethyl-2-methylthiocycloheptimidazolium trifluoromethanesulfonate and 3.4 g of 3-ethyl-2-ethylthiobenzothiazolium p-toluenesulfonate were added to 50 ml of acetonitrile, and 2.4 ml of triethylamine was added thereto and everything was stirred under heating at an internal temperature of 45° C. for 1 hour. After the reaction, 200 ml of ethyl acetate was added, and the crystals precipitated were separated by filtration. The crystals were added to 100 ml of methanol, heated and dissolved, and then the insoluble substance was filtered out while hot. Next, a methanol solution (10 ml) containing 1.5 g of sodium iodide was added to the resulting filtrate and such was allowed to cool. The crystals precipitated were separated by filtration, washed with methanol and water and then dried.

1.5 g of violet crystals were obtained.
Yield: 35.9%. m.p.: 260° to 264° C.

EXAMPLE 12

Production of Dye (14): Alternative to Example 2

3 g of 3,6-dimethyl-2-methylthiocycloheptimidazolium trifluoromethanesulfonate and 3.3 g of 3-ethyl-2-ethylthiobenzoxazolium p-toluenesulfonate were added to 50 ml of acetonitrile, and 2.4 ml of triethylamine was added thereto and everything was stirred under heating at an internal temperature of 40° C. for 1 hour. After the reaction, 200 ml of ethyl acetate was added, and the crystals precipitated were separated by filtration. The crystals were added to 150 ml of methanol, heated and dissolved, and then the insoluble substance was filtered out while hot. A methanol solution (10 ml) containing 1.5 g of potassium iodide was added to the resulting filtrate and then such was allowed to cool.

The crystals thus precipitated were separated by filtration, washed with methanol and water and then dried.

2.4 g of violet crystals were obtained.
Yield: 59%. m.p.: 300° C. or higher.

EXAMPLE 13

Production of Dye (46)

3 g of 3,6-dimethyl-2-methylthiocycloheptimidazolium trifluoromethanesulfonate and 5 g of 2-(2-acetanilidovinyl)-3-ethylbenzothiazolium p-toluenesulfonate were added to 50 ml of methanol, and 2.4 ml of triethylamine was added thereto and everything was stirred for 2 hours at room temperature. Next, a methanol solution (10 ml) containing 1 g of sodium iodide was added and further stirred for a while, whereby crystals precipitated out. These crystals were separated by filtration and added to 200 ml of methanol and dissolved by heating under reflux. The insoluble substance was filtered out while hot, and the filtrate was allowed to cool. The crystals precipitated were separated by filtration, washed with methanol and then dried.

2.5 g of violet crystals were obtained.
Yield: 56.8%. m.p.: 215° to 216° C.
$\lambda_{max} = 672$ nm ($\epsilon = 1.02 \times 10^5$) (methanol solvent).

EXAMPLE 14

Production of Dye (59)

3 g of 3,6-dimethyl-2-methylthiocycloheptimidazolium trifluoromethanesulfonate, as obtained in Example 11-(d), and 3.1 g of 5-(acetanilidomethylidene)-3-ethylrhodanine were added to 100 ml of methanol, and 2.4 ml of triethylamine was added thereto and stirred for 1 hour at room temperature.

The crystals were separated by filtration and added to 200 ml of methanol and dissolved therein by heating under reflux. The insoluble substance was filtered out while hot, and the resulting filtrate was allowed to cool. The crystals precipitated were separated by filtration, washed with methanol and dried.

2.1 g of a violet crystal was obtained.
Yield: 66.0%. m.p.: 151° to 152° C.
$\lambda_{max} = 621$ nm ($\epsilon = 5.20 \times 10^4$) (methanol solvent).

EXAMPLE 15

Production of Dye (45): Alternative to Example 13

The production of Dye (45) is explained below in order from the preparation of the raw materials.

(a) Production of
6-(2-Acetanilidovinyl)-3-methyl-2-methylthiocycloheptimidazolium trifluoromethanesulfonate 10 g of 3,6-dimethyl-2-methylthiocycloheptimidazolium trifluoromethanesulfonate, as obtained in Example 11-(d), and 8.3 g of N,N'-diphenylformamidine were added to 150 ml of acetic anhydride and everything was stirred under heating at an internal temperature of about 90° C. for 1 hour. After allowing such to cool, 150 ml of ethyl acetate was added, and the crystals precipitated were separated by filtration and dried.

12 g of yellow crystals were obtained.
Yield: 85.1%. m.p.: 162° to 163° C.

(b) Production of Dye (46)

4 g of 6-(2-acetanilidovinyl)-3-methyl-2-methylthiocycloheptimidazolium trifluoromethanesulfonate and 2.5 g of 3-ethyl-2-methylbenzothiazolium p-toluenesulfonate were added to 50 ml of methanol, and 2.2 ml of triethylamine was added thereto and everything was stirred for 1 hour at room temperature. The subsequent steps were the same as Example 13.

2.7 g of violet crystals were obtained.
Yield: 73.0%. m.p.: 215° to 216° C.

EXAMPLE 16

Production of Dye (59): Alternative to Example 14

4 g of 6-(2-acetanilidovinyl)-3-methylthiocycloheptimidazolium trifluoromethanesulfonate, as obtained in Example 15-(a) and 1.16 g of 3-ethylrhodanine were added to 100 ml of methanol, and 2.2 ml of triethylamine was added thereto and everything was stirred for 1 hour at room temperature.

The subsequent steps were the same as Example 14.
2.3 g of violet crystals were obtained.
Yield: 85.2%. m.p.: 151° to 152° C.

EXAMPLE 17

Production of Dye (72)

5 g of 3,6-dimethyl-2-methylthiocycloheptimidazolium trifluoromethanesulfonate, as obtained in Example 11-(d), 1.66 g of N,N'-diphenylformamidine and 2 ml of acetic anhydride were added to 100 ml of methanol, and 3.9 ml of triethylamine was added thereto and everything was stirred for 1 hour at room temperature. Next, a methanol solution (10 ml) containing 1 g of sodium iodide was added to the resulting reaction solution. After stirring for a while, the crystals precipitated were separated by filtration, and this was dissolved in 100 ml of methanol by heating under reflux, and the insoluble substance was filtered out while hot. The resulting filtrate was allowed to cool, and the crystals thus precipitated were separated by filtration, washed with methanol and then dried.

2.1 g of violet crystals were obtained.
Yield: 54.5%. m.p.: 140° to 141° C.
$\lambda_{max} = 825$ nm ($\epsilon = 1.21 \times 10^5$) (methanol solvent).

Determination of Structure

All the dyes of the present invention, as produced in the above-described Examples 1 to 17 showed a molecular ion (parent) peak in the mass-spectrography. In addition, the experimental elementary analysis data were found to correspond to the respective theoretical values in each of the dyes formed.

$^1$H-NMR data for some of the dyes obtained in the examples are shown below. (In every case, the measurement was effected by 400 MHz-$^1$H-NMR with DMSO-D$^6$ solvent.)

(1): Temperature of measurement: 298K

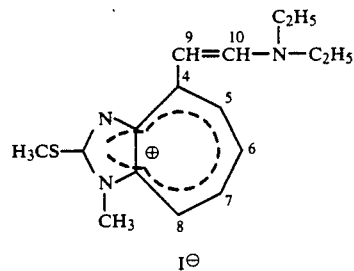

δppm, J in Hz: 1.23 (3H, t, J=8, N—CH$_2$—CH$_3$), 1.26 (3H, t, J=8, N—CH$_2$—CH$_3$), 2.77 (3H, s, S—CH$_3$), 3.60 (2H, q, J=8, NCH$_2$CH$_3$), 3.65 (2H, q, N—CH$_2$CH$_3$), 3.73 (3H, s, N—CH$_3$), 6.07 (1H, d, J=13, H-10), 7.36 (1H, t, J=12, H-7), 7.67 (1H, d, J=12, H-5), 7.75 (1H, t, J=12, H-6), 7.91 (1H, d, J=12, H-8), 8.50 (1H, t, J=13, H-9).

(6): Temperature of measurement: 373K

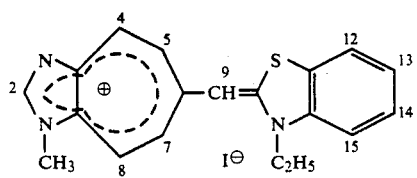

δppm, J in Hz: 1.45 (3H, t, J=8, N—CH$_2$—CH$_3$), 3.93 (3H, s, N—CH$_3$), 4.67 (2H, q, J=8, N—CH$_2$CH$_3$), 6.90 (1H, s, H-9), 7.55–7.66 (4H, m, H-13 (or 14), 3H among H-4, 5, 7, 8), 7.73 (1H, td, J=8, 0.5, H-1, 4 (or 13)), 7.83 (1H, dd, J=12, 1, 1H among H-4, 5, 7, 8), 7.95 (1H, d, J=8, H-15), 8.17 (1H, d, J=8, H-12), 8.33 (1H, s, H-2).

(7): Temperature of Measurement: 333K

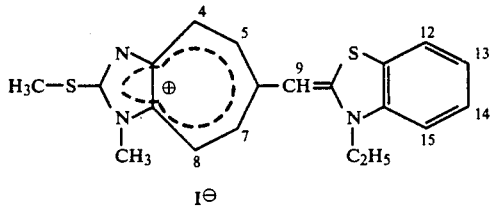

δppm, J in Hz: 1.41 (3H, t, J=8, N—CH₂C$\underline{H}_3$), 2.79 (3H, s, S—C$\underline{H}_3$), 3.78 (3H, s, N—C$\underline{H}_3$), 4.62 (2H, q, J=8, N—C$\underline{H}_2$CH₃), 6.88 (1H, s, H-9), 7.54 (1H, t, J=8, H-14 (or 13)), 7.67 (2H, d, J=12, H-5, 7 (or 4, 8)), 7.69 (1H, t, J=8, H-13 (or 14)), 7.88 (2H, d, J=12, H-4, 8 (or 5, 7)), 7.90 (1H, d, J=8, H-15), 8.14 (1H, d, J=8, H-12).

(14): Temperature of measurement: 373K

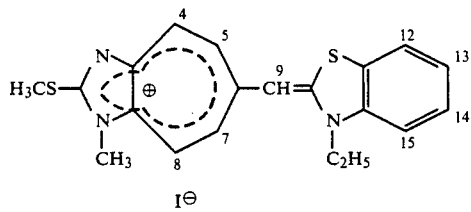

δppm, J in Hz: 1.44 (3H, t, J=7, N—CH₂C$\underline{H}_3$), 2.79 (3H, s, S—C$\underline{H}_3$), 3.79 (3H, s, N—C$\underline{H}_3$), 4.38 (2H, q, J=7, N—C$\underline{H}_2$CH₃), 6.22 (1H, s, H-9), 7.48 (1H, td, J=8, 1, H-14 (or 13)), 7.54 (1H, td, J=8, 1, H-13 (or 14)), 7.73 (1H, dd, J=8, 1, H-15), 7.79 (1H, dd, J=8, 1, H-12), 7.85–7.89 (2H, m, H-5, 7 (or 4, 8)), 7.91–8.02 (2H, bm, H-4, 8 (or 5, 7)).

(30): Temperature of measurement: 323K

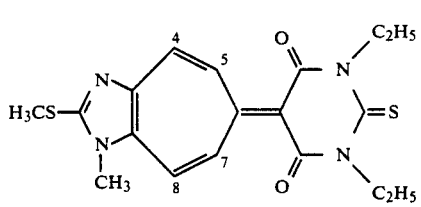

δppm, J in Hz: 1.20 (6H, t, J=8, N—CH₂C$\underline{H}_3$), 2.86 (3H, s, —SC$\underline{H}_3$), 3.88 (3H, s, N—C$\underline{H}_3$), 4.48 (4H, q, J=8, NC$\underline{H}_2$CH₃), 8.43 (1H, d, J=12, H-5 or 7 (or 4 or 8)), 8.46 (1H, d, J=12, H-5 or 7 (or 4 or 8)), 9.17 (1H, d, J=12, H-4 or 8 (or 5 or 7)), 9.20 (1H, d, J-12, H-4 or 8 (or 5 or 7).

(31): Temperature of measurement: 323K

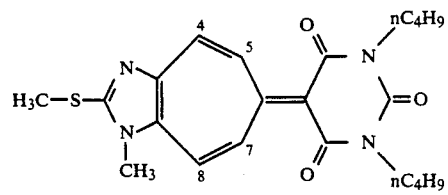

δppm, J in Hz: 0.89 (6H, t, J=8, —N(CH₂)₃C$\underline{H}_3$), 1.28 (4H, qt, J=8, NCH₂CH₂C$\underline{H}_2$CH₃), 1.52 (4H, tt, J=8, NCH₂C$\underline{H}_2$CH₂CH₃), 2.82 (3H, s, —SCH₃), 3.83 (3H, s, —NCH₃), 3.83 (4H, t, J=8, NC$\underline{H}_2$CH₂CH₂CH₃), 8.23 (1H, d, J=12, H-5 or 7 (or 4 or 8)), 8.25 (1H, d, J=12, H-5 or 7 (or 4 or 8)), 9.18 (1H, d, J=12, H-4 or 8 (or 5 or 7)), 9.22 (1H, d, J=12, H-4 or 8 (or 5 or 7)).

(39): Temperature of measurement: 373K

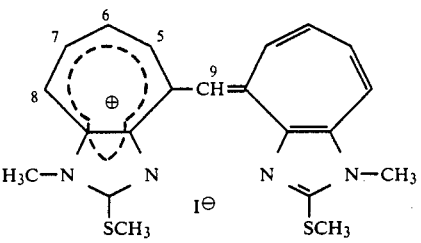

δppm, J in Hz: 2.84 (6H, s, —SC$\underline{H}_3$), 3.82 (6H, s, N—C$\underline{H}_3$), 7.36 (2H, t, J=12, H-7), 7.47 (2H, t, J=12, H-6), 7.84 (2H, d, J=12, H-5), 8.22 (2H, d, J=12, H-8), 8.44 (1H, s, H-9).

In addition, nuclear overhawser effect (NOE) was observed between N—CH₃ and H-8.

(68): Temperature of measurement: 373K

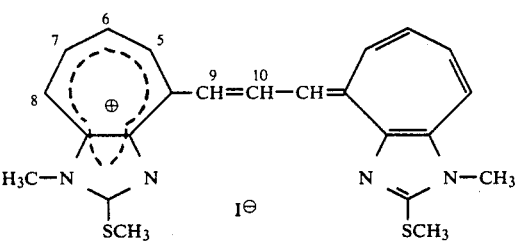

δppm, J in Hz: 2.88 (6H, s, —SC$\underline{H}_3$), 3.77 (6H, s, N—C$\underline{H}_3$), 7.19 (2H, t, J=12, H-7), 7.27 (2H, t, J=12, H-6), 7.33 (2H, d, J=13, H-9), 7.66 (2H, d, J=12, H-5), 8.18 (2H, d, J=12, H-8), 9.10 (1H, bt, J=13, H-10).

EXAMPLE 18

Production of Dye (104)

2.8 g of 3-methyl-2-methylthiocycloheptimidazolium trifluoromethanesulfonate and 2.83 g of 1-ethyl-2-methylquinolium p-toluenesulfonate were added to 50 ml of acetonitrile, and after further adding thereto 2.3 ml of triethylamine, the mixture was heated under reflux for one hour. The solvent was distilled off under reduced pressure, and the residue was purified by silica gel column chromatography with a developer of a mixed solvent of methanol/chloroform (=¼ by volume). The crystals thus obtained were added to 50 ml of methanol and dissolved therein under heating. After the insoluble substance was filtered out while hot, a methanol solution (3 ml) containing 1.2 g of sodium iodide was added to the resulting filtrate, followed by allowing the mixture to stand for cooling. The crystals precipitated were separated by filtration, washed with methanol and water, and then dried. 0.7 g of violet crystals were obtained.

Yield: 18%. m.p.: 280° C. or higher.
$\lambda_{max} = 597$ nm ($\epsilon = 1.05 \times 10^5$) (methanol solvent).

In the production of this dye, a slight amount of a dye having substituents at the 4- and 8-positions on the cyclopeptimidazole nucleus was obtained as a by-product dye.

In each of the subsequent examples, a similar by-product dye was obtained.

EXAMPLE 19

Production of Dye (119)

The same procedures as in Example 18 were followed, except that 2.83 g of 1-ethyl-4-methylquinolium p-toluenesulfonate was used in place of the 1-ethyl-2-methylquinolium p-toluenesulfonate. 0.6 g of violet crystals were obtained.

Yield: 15%. m.p.: 250° to 260° C.
$\lambda_{max} = 648$ nm ($\epsilon = 9.51 \times 10^4$) (methanol solvent).

EXAMPLE 20

Production of Dye (118)

The same procedures as in Example 18 were followed, except that 2.4 g of 1-ethyl-4-methylpyridinium p-toluenesulfonate was used in place of the 1-ethyl-2-methylquinolium p-toluenesulfonate. 0.43 g of violet crystals were obtained.

Yield: 12%. m.p.: 280° C. or higher.
$\lambda_{max} = 598$ nm ($\epsilon = 8.80 \times 10^4$) (methanol solvent).

EXAMPLE 21

Production of Dye (104): Alternative to Example 18

3 g of 3,6-dimethyl-2-methylthiocycloheptimidazolium trifluoromethanesulfonate and 3.4 g of 1-ethyl-2-ethylthioquinolium p-toluenesulfonate were added to 50 ml of acetonitrile, and 2.4 ml of triethylamine was further added thereto and everything was stirred under heating at an internal temperature of 45° C. for one hour. After the reaction, 200 ml of ethyl acetate was added, and the crystals precipitated were separated by filtration. The crystals were added to 100 ml of methanol, heated and dissolved, and then the insoluble substance was filtered out while hot. A methanol solution (10 ml) containing 1.5 g of potassium iodide was added to the resulting filtrate and then such was allowed to cool.

The crystals thus precipitated were separated by filtration, washed with methanol and water, and then dried. 1.05 g of violet crystals were obtained.

Yield: 25%.

EXAMPLE 22

Production of Dye (119): Alternative to Example 19

3 g of 3,6-dimethyl-2-methylthiocycloheptimidazolium trifluoromethanesulfonate and 3.4 g of 3-ethyl-2-ethylthiobenzoxazolium p-toluenesulfonate were added to 50 ml of acetonitrile, and 2.4 ml of triethylamine was further added thereto and everything was stirred under heating at an internal temperature of 40° C. for one hour. After the reaction, 200 ml of ethyl acetate was added, and the crystals precipitated were separated by filtration. The crystals were added to 150 ml of methanol, heated and dissolved, and then the insoluble substance was filtered out while hot. A methanol solution (10 ml) containing 1.5 g of potassium iodide was added to the resulting filtrate and then such was allowed to cool.

The crystals thus precipitated were separated by filtration, washed with methanol and water, and then dried. 1.3 g of violet crystals were obtained.

Yield: 31%.

As is apparent from the above-described example, the present invention provides new methine dyes.

The methine dyes of the present invention show a long absorption with one or a few methine bonds and have high light-stability and solution-stability.

The methine dyes of the present invention display a higher level of stability and an absorption peak of a relatively longer wavelength than those as expected on the basis of the number of the methine groups in the chromophoric group. These advantages result from the presence of the 1-substituted cycloheptimidazole nucleus in the dye.

Since the methine dyes of the present invention has a stability of a high level, these can be used in various fields of photographic dyes (e.g., sensitizing dyes, desensitizing dyes, filter dyes, etc.), dyes for optical discs, electrophotographic dyes, optical filters, etc.

While the invention has been described in detail and with reference to specific embodiments thereof, it will be apparent to one skilled in the art that various changes and modifications can be made therein without departing from the spirit and scope thereof.

What is claimed is:

1. A methine dye of formula (I) in which the 7-membered ring moiety of the nucleus is substituted by a methine bond having an auxochrome, at its terminal, for forming a conjugated resonance chromophoric group with the 10 π electron series of the nucleus.

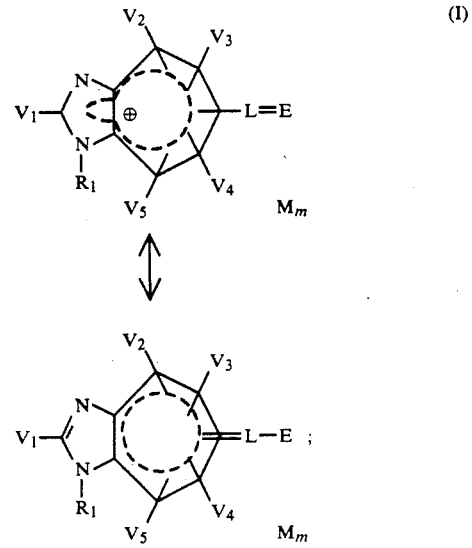

and in which

E represents an auxochrome;
L represents a methine bond;

$R_1$ represents a substituted or unsubstituted alkyl group, a substituted or unsubstituted aryl group or a substituted or unsubstituted heterocyclic ring;

the methine bond being an unsubstituted or substituted methine group;

$V_1$, $V_2$, $V_3$, $V_4$ and $V_5$ independently represent a hydrogen atom, a halogen atom, or a substituted or unsubstituted alkyl group, a substituted or unsubstituted acyl group, a substituted or unsubstituted acyloxy group, a substituted or unsubstituted alkoxycarbonyl group, a substituted or unsubstituted carbamoyl group, a substituted or unsubstituted sulfamoyl group, a carboxyl group, a cyano group, a hydroxyl group, a substituted or unsubstituted amino group, a substituted or unsubstituted acylamino group, a substituted or unsubstituted alkoxy group, a substituted or unsubstituted alkylthio group, a substituted or unsubstituted alkylsulfonyl group, a sulfonic acid group or a substituted or unsubstituted aryl group, or two of $V_1$ to $V_5$ which are bonded to the adjacent carbon atoms may form a condensed ring;

M represents an electric charge-equilibrating paired ion;

m represents 0 or 1; and the methine bond can be in the 4-, 5-, 6-, 7- or 8-position.

2. A methine dye of formula (I) in which the 7-membered ring moiety of the nucleus is substituted by a methine bond having an auxochrome, at its terminal, for forming a conjugated resonance chromophoric group with the 10 $\pi$ electron series of the nucleus:

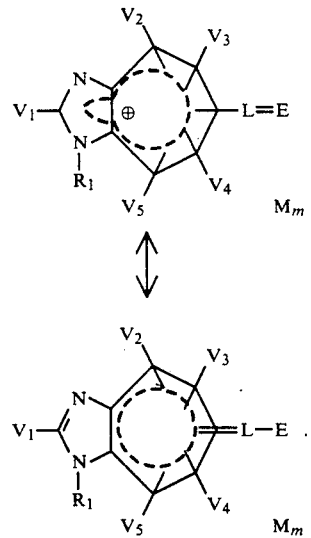

(I)

in which

E represents an auxochrome;

L represents a methine bond;

$R_1$ represents a substituted or unsubstituted alkyl group, a substituted or unsubstituted aryl group or a substituted or unsubstituted 5-membered heterocyclic ring;

the methine bond being an unsubstituted or substituted methine group;

$V_1$, $V_2$, $V_3$, $V_4$ and $V_5$ independently represent a hydrogen atom, a halogen atom, or a substituted or unsubstituted alkyl group, a substituted or unsubstituted acyl group, a substituted or unsubstituted acyloxy group, a substituted or unsubstituted alkoxycarbonyl group, a substituted or unsubstituted carbamoyl group, a substituted or unsubstituted sulfamoyl group, a carboxyl group, a cyano group, a hydroxyl group, a substituted or unsubstituted amino group, a substituted or unsubstituted acylamino group, a substituted or unsubstituted alkoxy group, a substituted or unsubstituted alkylthio group, a substituted or unsubstituted alkylsulfonyl group, a sulfonic acid group or a substituted or unsubstituted aryl group, or two of $V_1$ to $V_5$ which are bonded to the adjacent carbon atoms may form a condensed ring;

M represents an electric charge-equilibrating paired ion;

m represents 0 or 1; and the methine bond can be in the 4-, 5-, 6-, 7- or 8-position.

3. A methine dye as in claim 2, which is represented by the formula (III):

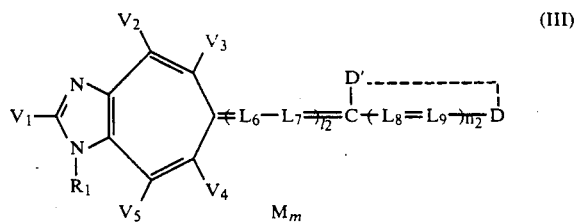

(III)

in which $R_1$, $V_1$ to $V_5$, M and m have the same meanings as in claim 2;

the position of the methine bond may be any of the 4-, 5-, 6-, 7- or 8-position;

D and D' each represents an atomic group necessary for forming an acidic nucleus, which may be acyclic or cyclic;

$L_6$, $L_7$, $L_8$ and $L_9$ have the same meanings as $L_1$, $L_2$, $L_3$, $L_4$ and $L_5$;

$l_2$ represents an integer of from 0 to 3; and $n_2$ represents 0 to 1.

4. A methine dye as in claim 2, which is represented by the formula (IV):

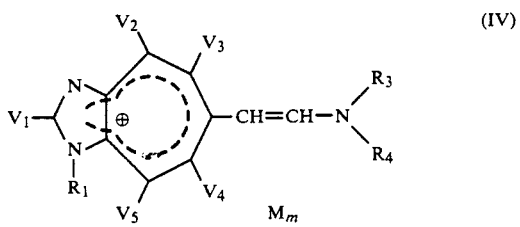

(IV)

in which $R_1$, $V_1$ to $V_5$, M and m have the same meanings as in claim 2;

the position of the methine bond may be any of the 4-, 5-, 6-, 7- or 8-position; and $R_3$ and $R_4$ independently represents a substituent for tertiary amines.

5. A methine dye as in claim 2, which is represented by the formula (V):

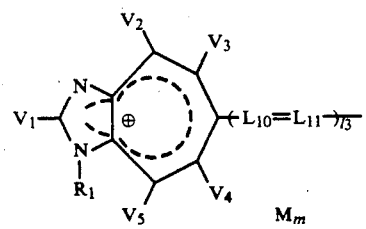

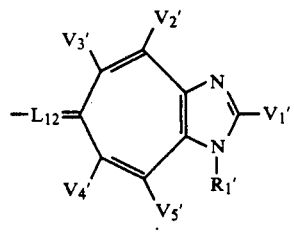

in which $R_1$, $V_1$ to $V_5$, M and m have the same meanings as in claim 2;

$R_1'$ has the same meaning as $R_1$;

$V_1'$ to $V_5'$ have the same meanings as $V_1$ to $V_5$;

the position of the methine bond may be any of the 4-, 5-, 6-, 7- or 8-position;

$L_{10}$, $L_{11}$ and $L_{12}$ have the same meanings as $L_1$, $L_2$, $L_3$, $L_4$ and $L_5$; and $l_3$ represents an integer of from 0 to 3.

6. A methine dye as in claim 2, which is represented by the formula (II):

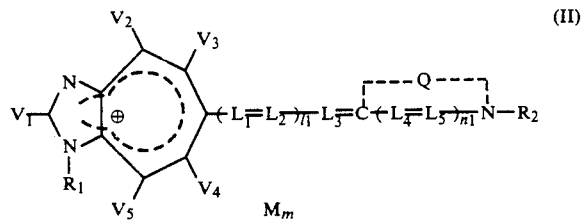

(II)

in which $R_1$, $V_1$ to $V_5$, M and m have the same meanings as in claim 2;

the position of the methine bond may be any of the 4-, 5-, 6-, 7- or 8-position;

Q represents an atomic group necessary for forming a 5-membered nitrogen-containing hetero-ring;

$L_1$, $L_2$, $L_3$, $L_4$ and $L_5$ independently represents an unsubstituted or substituted methine group;

$R_2$ represents a substituted or unsubstituted alkyl group;

$l_1$ represents an integer of from 0 to 3; and $n_1$ represents 0 or 1.

7. A methine dye as in claim 2, wherein the substituents for $R_1$, $V_1$, $V_2$, $V_3$, $V_4$ and $V_5$ are independently selected from the group consisting of a carboxyl group, a sulfo group, a cyano group, a halogen atom, a hydroxyl group, an alkoxycarbonyl group having 8 or less carbon atoms, an alkoxy group having 8 or less carbon atoms, a monocyclic aryloxy group having 10 or less carbon atoms, an acyloxy group having 3 or less carbon atoms, an acyl group having 8 or less carbon atoms, a carbamoyl group, a sulfamoyl group and an aryl group.

8. A methine dye as in claim 6, wherein the substituents for $R_1$, $R_2$, $V_1$, $V_2$, $V_3$, $V_4$ and $V_5$ are independently selected from the group consisting of a carboxyl group, a sulfo group, a cyano group, a halogen atom, a hydroxyl group, an alkoxycarbonyl group having 8 or less carbon atoms, an alkoxy group having 8 or less carbon atoms, a monocyclic aryloxy group having 10 or less carbon atoms, an acyloxy group having 3 or less carbon atoms, an acyl group having 8 or less carbon atoms, a carbamoyl group, a sulfamoyl group and an aryl group.

9. A methine dye as in claim 4, wherein the substituents for $R_1$, $R_2$, $R_3$, $R_4$, $V_1$, $V_2$, $V_3$, $V_4$ and $V_5$ are independently selected from the group consisting of a carboxyl group, a sulfo group, a cyano group, a halogen atom, a hydroxyl group, an alkoxycarbonyl group having 8 or less carbon atoms, an alkoxy group having 8 or less carbon atoms, a monocyclic aryloxy group having 10 or less carbon atoms, an acyloxy group having 3 or less carbon atoms, an acyl group having 8 or less carbon atoms, a carbamoyl group, a sulfamoyl group and an aryl group.

10. A methine dye as in claim 5, wherein the substituents for $R_1$, $V_1$, $V_2$, $V_3$, $V_4$, $V_5$, $R_{1'}$, $V_{1'}$, $V_{2'}$, $V_{3'}$, $V_{4'}$, and $V_{5'}$ are independently selected from the group consisting of a carboxyl group, a sulfo group, a cyano group, a halogen atom, a hydroxyl group, an alkoxycarbonyl group having 8 or less carbon atoms, an alkoxy group having 8 or less carbon atoms, a monocyclic aryloxy group having 10 or less carbon atoms, an acyloxy group having 3 or less carbon atoms, an acyl group having 8 or less carbon atoms, a carbamoyl group, a sulfamoyl group and an aryl group.

* * * * *